(12) United States Patent
Curran et al.

(10) Patent No.: US 10,384,187 B2
(45) Date of Patent: Aug. 20, 2019

(54) COMPOSITE LIQUID CELL (CLC) MEDIATED NUCLEIC ACID LIBRARY PREPARATION DEVICE, AND METHODS FOR USING THE SAME

(71) Applicant: GenCell Biosystems Ltd., Raheen, County Limerick (IE)

(72) Inventors: Kieran Curran, Ballyclough (IE); Brian Chawke, Askeaton (IE); Noel Sirr, Ballymoe (IE)

(73) Assignee: GENCELL BIOSYSTEMS LTD, Raheen, County Limerick (IE)

( * ) Notice: Subject to any disclaimer, the term of this patent is extended or adjusted under 35 U.S.C. 154(b) by 0 days.

(21) Appl. No.: 14/617,704

(22) Filed: Feb. 9, 2015

(65) Prior Publication Data

US 2015/0238920 A1    Aug. 27, 2015

Related U.S. Application Data

(60) Provisional application No. 61/937,879, filed on Feb. 10, 2014.

(51) Int. Cl.
*B01J 19/00*  (2006.01)
*C12Q 1/68*  (2018.01)
*C12N 15/10*  (2006.01)
*C12Q 1/6874*  (2018.01)

(52) U.S. Cl.
CPC ...... *B01J 19/0046* (2013.01); *C12N 15/1065* (2013.01); *B01J 2219/00317* (2013.01); *B01J 2219/00367* (2013.01); *B01J 2219/00369* (2013.01); *B01J 2219/00416* (2013.01); *B01J 2219/00484* (2013.01); *B01J 2219/00495* (2013.01); *B01J 2219/00529* (2013.01); *B01J 2219/00547* (2013.01); *B01J 2219/00587* (2013.01); *B01J 2219/00596* (2013.01); *B01J 2219/00608* (2013.01); *B01J 2219/00659* (2013.01); *B01J 2219/00691* (2013.01); *B01J 2219/00722* (2013.01); *C12Q 1/6874* (2013.01)

(58) Field of Classification Search
None
See application file for complete search history.

(56) References Cited

U.S. PATENT DOCUMENTS

| 3,783,696 | A | | 1/1974 | Coleman |
| 3,952,599 | A | | 4/1976 | Ayres |
| 3,958,045 | A | | 5/1976 | Coleman |
| 4,962,395 | A | * | 10/1990 | Baird ................. G01F 23/2925 |
| | | | | 250/577 |
| 5,059,398 | A | | 10/1991 | Kenney |
| 5,221,518 | A | | 6/1993 | Mills |
| 5,408,306 | A | | 4/1995 | Anderson |
| 5,474,796 | A | | 12/1995 | Brennan |
| 5,486,337 | A | | 1/1996 | Ohkawa |
| 5,505,877 | A | | 4/1996 | Krivohlavek |
| 5,639,426 | A | | 6/1997 | Kerr et al. |
| 5,679,460 | A | | 10/1997 | Schakenraad et al. |
| 5,980,936 | A | | 11/1999 | Krafft et al. |
| 6,136,609 | A | | 10/2000 | Sato et al. |
| 6,284,546 | B1 | | 9/2001 | Bryning et al. |
| 6,326,211 | B1 | | 12/2001 | Anderson et al. |
| 6,640,891 | B1 | * | 11/2003 | Oldenburg .......... B01L 3/50851 |
| | | | | 165/253 |
| 7,129,091 | B2 | | 10/2006 | Ismagliov et al. |
| 7,138,233 | B2 | | 11/2006 | Griffiths et al. |
| 7,238,323 | B2 | | 7/2007 | Knapp et al. |
| 7,244,396 | B2 | | 7/2007 | Chait et al. |
| 7,244,567 | B2 | | 7/2007 | Chen et al. |
| 7,252,943 | B2 | | 8/2007 | Griffiths et al. |
| 7,323,305 | B2 | | 1/2008 | Leamon et al. |
| 7,329,545 | B2 | | 2/2008 | Pamula et al. |
| 7,439,014 | B2 | | 10/2008 | Pamula et al. |
| 7,582,446 | B2 | | 9/2009 | Griffiths et al. |
| 7,597,809 | B1 | | 10/2009 | Roberts |
| 7,638,276 | B2 | | 12/2009 | Griffiths et al. |
| 7,759,132 | B2 | | 7/2010 | Pollack et al. |
| 7,776,927 | B2 | | 8/2010 | Chu et al. |
| 7,842,457 | B2 | | 11/2010 | Berka et al. |
| 7,901,939 | B2 | | 3/2011 | Ismagliov et al. |
| 7,915,013 | B2 | | 3/2011 | Cho et al. |
| 7,943,348 | B2 | | 5/2011 | Cho et al. |
| 8,029,744 | B2 | | 10/2011 | Noda et al. |
| 8,128,798 | B2 | | 3/2012 | Adachi et al. |
| 8,158,359 | B2 | | 4/2012 | Leamon et al. |
| 8,252,539 | B2 | | 8/2012 | Quake et al. |
| 8,256,308 | B2 | | 9/2012 | Buechner |
| 8,263,023 | B2 | | 9/2012 | Le Vot et al. |
| 8,273,573 | B2 | | 9/2012 | Ismagliov et al. |
| 8,304,193 | B2 | | 11/2012 | Ismagliov et al. |
| 8,329,407 | B2 | | 12/2012 | Ismagliov et al. |
| 8,367,326 | B2 | | 2/2013 | Griffiths et al. |
| 8,709,762 | B2 | | 4/2014 | Hindson |
| 8,748,102 | B2 | | 6/2014 | Berka et al. |
| 8,765,380 | B2 | | 7/2014 | Berka et al. |
| 8,790,876 | B2 | | 7/2014 | Leamon et al. |
| 9,194,772 | B2 | | 11/2015 | Lee et al. |
| 9,277,759 | B2 | | 3/2016 | Bibette et al. |
| 9,776,182 | B2 | | 10/2017 | Curran et al. |

(Continued)

FOREIGN PATENT DOCUMENTS

CN    1785496 A    6/2006
CN    101028607 A    9/2007

(Continued)

OTHER PUBLICATIONS

Meldrum et al. (Genome Research 10.8 (2000): 1081-1092.).*

(Continued)

*Primary Examiner* — Tracy Vivlemore
*Assistant Examiner* — Sahana S Kaup
(74) *Attorney, Agent, or Firm* — Kathleen Y. Rao; Bret E. Field; Bozicevic, Field & Francis LLP

(57) ABSTRACT

Complete nucleic acid library preparation devices are provided. Aspects of the devices include: a thermal chip module comprising multiple nodes; one or more plate locations; a robotically controlled liquid handler configured to transfer liquid between the one or more plate locations and the thermal chip module; and a bulk reagent dispenser configured to access each node of the thermal chip module.

22 Claims, 10 Drawing Sheets

(56) References Cited

U.S. PATENT DOCUMENTS

| | | | |
|---|---|---|---|
| 2001/0039014 A1 | 11/2001 | Bass et al. | |
| 2002/0009392 A1 | 1/2002 | Wolk et al. | |
| 2002/0050659 A1 | 5/2002 | Toreki et al. | |
| 2003/0032198 A1 | 2/2003 | Lugmair et al. | |
| 2004/0096365 A1* | 5/2004 | Toi | G01N 35/1011 422/502 |
| 2004/0203174 A1 | 10/2004 | Jones et al. | |
| 2005/0087122 A1 | 4/2005 | Ismagliov et al. | |
| 2005/0221370 A1* | 10/2005 | Hodge | G01N 35/00871 435/6.11 |
| 2006/0083660 A1* | 4/2006 | Schorno | G01N 35/02 422/63 |
| 2006/0246224 A1 | 11/2006 | Neitzel | |
| 2007/0026421 A1* | 2/2007 | Sundberg | B01L 3/5027 435/6.12 |
| 2007/0037294 A1 | 2/2007 | Pamula et al. | |
| 2007/0042367 A1 | 2/2007 | Tao et al. | |
| 2007/0243634 A1 | 10/2007 | Pamula et al. | |
| 2007/0275415 A1 | 11/2007 | Srinivasan et al. | |
| 2008/0023330 A1 | 1/2008 | Viovy et al. | |
| 2008/0224086 A1 | 9/2008 | Falkowski et al. | |
| 2009/0023189 A1 | 1/2009 | Lau et al. | |
| 2009/0042281 A1 | 2/2009 | Chang et al. | |
| 2009/0131543 A1 | 5/2009 | Weitz et al. | |
| 2009/0260458 A1 | 10/2009 | Joseph et al. | |
| 2009/0275113 A1* | 11/2009 | Maltezos | B01L 3/50851 435/286.1 |
| 2010/0015614 A1 | 1/2010 | Beer et al. | |
| 2010/0016452 A1 | 1/2010 | Nedwed et al. | |
| 2010/0022414 A1 | 1/2010 | Link et al. | |
| 2010/0096342 A1 | 4/2010 | Roberts | |
| 2010/0105112 A1 | 4/2010 | Holtze et al. | |
| 2010/0120635 A1 | 5/2010 | Davies et al. | |
| 2010/0173394 A1 | 7/2010 | Colston, Jr. et al. | |
| 2010/0267585 A1* | 10/2010 | Terbrueggen | C12Q 1/6855 506/16 |
| 2011/0120937 A1 | 5/2011 | Ishizuka et al. | |
| 2011/0171748 A1 | 7/2011 | Cox et al. | |
| 2011/0212516 A1 | 9/2011 | Ness et al. | |
| 2012/0028342 A1 | 2/2012 | Ismagliov et al. | |
| 2012/0045765 A1* | 2/2012 | Curran | B01F 13/0071 435/6.12 |
| 2012/0208241 A1 | 8/2012 | Link | |
| 2012/0276543 A1 | 11/2012 | Quake et al. | |
| 2012/0276544 A1 | 11/2012 | Quake et al. | |
| 2012/0298205 A1 | 11/2012 | Schertzer et al. | |
| 2013/0109575 A1 | 5/2013 | Kleinschmidt et al. | |
| 2013/0190189 A1 | 7/2013 | Griffiths et al. | |
| 2014/0113300 A1 | 4/2014 | Samuels | |
| 2014/0162885 A1 | 6/2014 | Berka et al. | |
| 2014/0199730 A1 | 7/2014 | Agresti et al. | |
| 2014/0199731 A1 | 7/2014 | Agresti et al. | |

FOREIGN PATENT DOCUMENTS

| | | | |
|---|---|---|---|
| CN | 101530444 A | 9/2009 | |
| CN | 102316989 A | 1/2012 | |
| CN | 1369698 A | 9/2012 | |
| DE | 10039195 A1 | 2/2002 | |
| EP | 1019496 B1 | 7/2000 | |
| EP | 1053784 A2 | 11/2000 | |
| EP | 0892035 B1 | 10/2004 | |
| EP | 1485204 B1 | 2/2006 | |
| EP | 1496120 B1 | 3/2007 | |
| EP | 1482036 B1 | 10/2007 | |
| EP | 1508044 B1 | 9/2010 | |
| EP | 1801214 B1 | 11/2010 | |
| EP | 2258846 A2 | 12/2010 | |
| EP | 2278337 A2 | 1/2011 | |
| EP | 2248578 B1 | 6/2012 | |
| EP | 1908832 B1 | 12/2012 | |
| EP | 2703497 A1 | 3/2014 | |
| JP | 6-506713 A | 7/1994 | |
| JP | 9-103662 A | 4/1997 | |
| JP | 2003236411 A | 8/2003 | |
| JP | 2008538077 A | 10/2008 | |
| JP | 2009534653 A | 9/2009 | |
| JP | 2010503516 A | 2/2010 | |
| JP | 2011-110474 A | 6/2011 | |
| WO | WO 93/03151 A1 | 2/1993 | |
| WO | 94/08759 A1 | 4/1994 | |
| WO | WO-0227035 A2 * | 4/2002 | C12N 15/1079 |
| WO | WO 2004/038363 A2 | 5/2004 | |
| WO | WO 2004069413 A1 | 8/2004 | |
| WO | WO 2005/002730 A1 | 1/2005 | |
| WO | WO 2007/024778 A2 | 3/2007 | |
| WO | WO 2007/024798 A2 | 3/2007 | |
| WO | WO 2007/024800 A2 | 3/2007 | |
| WO | WO 2007/024914 A2 | 3/2007 | |
| WO | 2007/120241 A2 | 10/2007 | |
| WO | WO 2008/130623 A1 | 10/2008 | |
| WO | WO 2008/144288 A1 | 11/2008 | |
| WO | WO 2009/061372 A1 | 5/2009 | |
| WO | WO/2009/061748 A1 | 5/2009 | |
| WO | WO 2009/134395 A1 | 11/2009 | |
| WO | WO 2009/149257 A1 | 12/2009 | |
| WO | WO 2010/063937 A1 | 6/2010 | |
| WO | WO 2010/104604 A1 | 9/2010 | |
| WO | WO 2010/121307 A1 | 10/2010 | |
| WO | WO 2012/011091 A2 | 1/2012 | |
| WO | WO2012024658 * | 2/2012 | |
| WO | WO-2012131556 A1 * | 10/2012 | B01L 3/502738 |
| WO | WO 2013/111016 A2 | 8/2013 | |
| WO | WO 2013/192351 A1 | 12/2013 | |
| WO | WO 2014/039587 A1 | 3/2014 | |
| WO | 2014/083435 A2 | 6/2014 | |
| WO | WO 2014/093714 A1 | 6/2014 | |
| WO | WO 2014/207577 A2 | 12/2014 | |

OTHER PUBLICATIONS

Lee et al. "On-chip procedures for magnetic particle-based assay in droplets", 16th International Conference on Miniaturized Systems for Chemistry and Life Sciences, Oct. 28-Nov. 1, 2012, Okinawa, Japan, pp. 347-349.

Lehmann et al. "A Lab-on-a-Chip using magnetic droplets", NSTI-Nanotech 2006, vol. 2, 2006, pp. 477-480.

Mastrobattista et al. "High-throughput screening of enzyme libraries: in vitro evolution of a beta-galactosidase by fluorescence-activated sorting of double emulsions", Chem Biol. Dec. 2005 12(12):1291-300.

Tawfik et al. "Man-made cell-like compartments for molecular evolution", Nat. Biotechnol. Jul. 1998; 16(7):652-6.

Utada et al. "Monodisperse Double Emulsions Generated from a Microcapillary Device", Science, Apr. 22, 2005, vol. 308, No. 5721, pp. 537-541.

Wu et al. "A double-emulsion microfluidic platform for in vitro green fluorescent protein expression", 2011 J. Micromech. Microeng. 21 054032, 7 pages.

BD Gencell, CLiC LP Overview Video, Feb. 19, 2014, 6 pages. Retrieved from the Internet, URL: https://www.youtube.com/watch?v=dxK4gHhIADA.

Gencell Biosystems Ltd., CLiC NGS Library Prep Brochure, Feb. 1, 2014, 2 pages. Retrieved online: http://cliclp.com/images/Documents_PDFs/GenCell_Biosystems_CLiC_LP_Overview_0214.pdf.

Yuzuki "Gen Cell Biosystems CLiC NGS Library liquid handler at AGBT 2014", Next Generation Technologist, Feb. 20, 2014, 6 pages. Retrieved online: http://www.yuzuki.org/gencell-biosystems-ngs-library-liquid-handler-agbt-2014/.

Notice of Reasons for Rejection, Japanese patent application No. 2015-543539, dated Apr. 3, 2018, 4 pages.

* cited by examiner

COMPOSITE LIQUID CELL (CLC) MEDIATED NUCLEIC ACID LIBRARY PREPARATION DEVICE, AND METHODS FOR USING THE SAME

CROSS-REFERENCE TO RELATED APPLICATIONS

Pursuant to 35 U.S.C. § 119 (e), this application claims priority to the filing date of U.S. Provisional Patent Application Ser. No. 61/937,879, filed Feb. 10, 2014, the disclosure of which application is incorporated herein by reference.

INTRODUCTION

Composite liquid cell (CLC) technology is a relatively recent platform technology that is highly suitable for carrying out precise biochemical reactions in small working volumes. A composition liquid cell is small volume roughly spherical structure having a core made up of an aqueous medium encapsulated by liquid shell of a medium immiscible with the core aqueous medium. In practice, the liquid cell is present on free surface of a third carrier fluid that is mutually immiscible with both the core and encapsulating mediums. A representation of a composite liquid cell (CLC) is provided in FIG. 1, which shows a core aqueous medium (sometimes referred to as a droplet reactor) encased in an encapsulating oil, where the resultant roughly spherical structure is present on a surface of a carrier oil that is immiscible with the encapsulating oil and the core aqueous medium. FIG. 2 provides a picture of a CLC.

One practical application of CLC technology is the production of nucleic acid libraries for next generation sequencing (NGS). Library preparation is a process by which a genomic nucleic acid sample is prepared for analysis via next generation sequencing. At present, next-generation platforms use slightly different methodologies such as pyrosequencing, sequencing by synthesis or sequencing by ligation. Most platforms, however, require nucleic acid preparations prior to sequencing. Typical steps include fragmentation (sonication, nebulization or shearing), followed by DNA repair and end polishing (blunt end or A overhang) and, finally, platform-specific adaptor ligation. Even for today's state-of-the-art sequencers a relatively high local concentration of the target molecule is required to sequence accurately. To streamline a particular workflow, automated machinery must overcome the challenges associated with automating and miniaturizing a series of processes aimed at modifying and amplifying nucleic acid content. This biochemistry process is generally performed in 96 or 384 static well plates with typical volumes ranging from 10 microliters to 200 microliters.

SUMMARY

Complete nucleic acid library preparation devices are provided. Aspects of the devices include: a thermal chip module comprising multiple nodes; one or more plate locations; a robotically controlled liquid handler configured to transfer liquid between the one or more plate locations and the thermal chip module; and a bulk reagent dispenser configured to access each node of the thermal chip module. The devices find use in, among other applications, CLC mediated nucleic acid library generation protocols, e.g., for use in next generation sequencing applications.

BRIEF DESCRIPTION OF THE FIGURES

The invention may be best understood from the following detailed description when read in conjunction with the accompanying drawings. Included in the drawings are the following figures.

DETAILED DESCRIPTION

Figure 1:
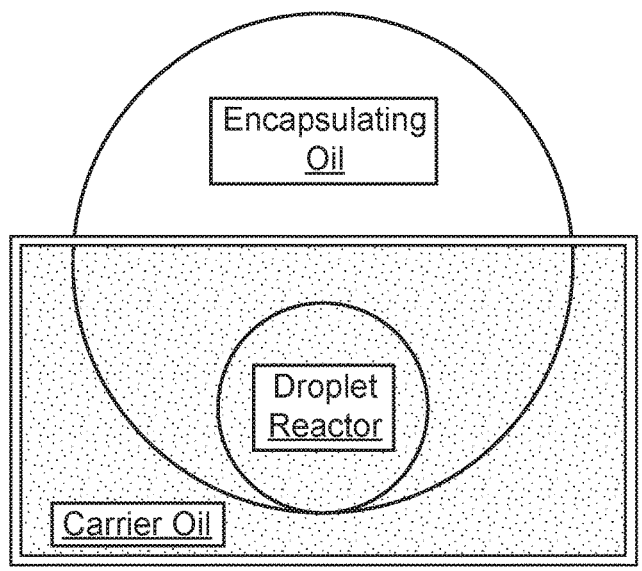
FIG. 1 provides a representation of a composite liquid cell (CLC).
Figure 2:
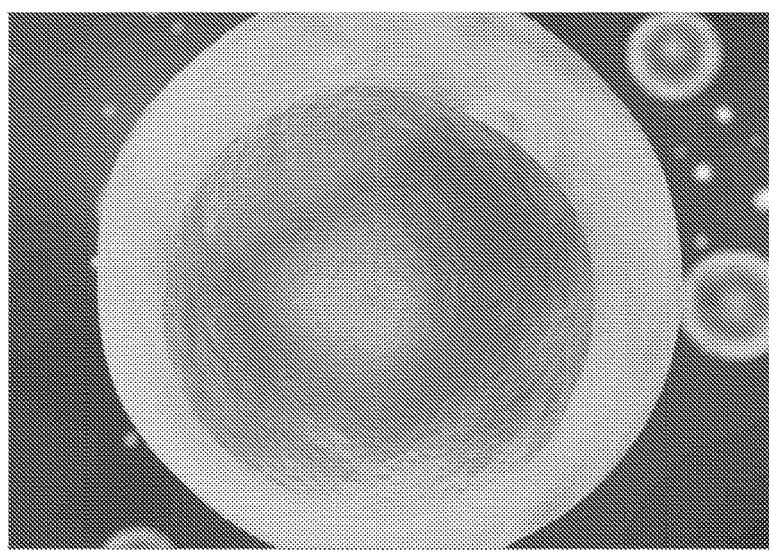
FIG. 2 provides a three-dimensional representation of a CLC.

Complete nucleic acid library preparation devices are provided. Aspects of the devices include: a thermal chip module comprising multiple nodes; one or more plate locations; a robotically controlled liquid handler configured to transfer liquid between the one or more plate locations and the thermal chip module; and a bulk reagent dispenser configured to access each node of the thermal chip module. The devices find use in, among other applications, CLC mediated nucleic acid library generation protocols, e.g., for use in next generation sequencing applications.

Before the present invention is described in greater detail, it is to be understood that this invention is not limited to particular embodiments described, as such may vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

Devices

As summarized above, aspects of the invention include a complete, compact nucleic acid NGS library preparation device. As the devices are complete nucleic acid library preparation devices, they include all components necessary to prepare a nucleic acid library suitable for next generation sequencing (NGS) from an initial nucleic acid sample. Accordingly, the devices are configured such that an initial nucleic acid sample can be introduced into the device and a complete nucleic acid library ready for use in a next generation sequencing protocol can be obtained from the device, with little if any user interaction with the device between the time of sample introduction and product NGS library retrieval. The devices include all liquid handling and other components necessary to produce an NGS nucleic acid library, as reviewed in greater detail below. The devices are automated, in that they are configured so that at least some, if not all, steps of a given library preparation protocol may occur without human intervention, beyond introduction of the nucleic acid sample into the device, loading of any requisite reagents and input of information, and activating the device to produce the nucleic acid library from the nucleic acid sample. Steps of a nucleic acid production protocol that may be automated in the devices include, but are not limited to: liquid transfer steps, reagent addition steps, thermal cycling steps, product purification steps, etc.

As indicated above, the devices are compact. By "compact" is meant that the device is dimensioned to be positioned on a bench top or table top in a research laboratory environment. In some instances the device has a length ranging from 0.5 to 4 meters, such as 1 to 2 meters, e.g., 1.54 meters; a width ranging from 0.25 to 1.75 meters, such as 0.5 to 1 meter, e.g., 0.805 meters; and a height ranging from 0.5 to 2 meters, such as 0.75 to 1.25 meters, e.g., 0.885 meters.

The weight of the device may vary, and in some instances ranges from 100 to 300 kg, such as 150 to 200 kg, e.g., 180 kg.

As summarized above, devices according to embodiments of the invention include at least a thermal chip module, one or more plate locations, a robotically controlled liquid handler configured to transfer liquid between the one or more plate locations the at least one thermal chip module and a bulk reagent dispenser configured to access each node of the at least one thermal chip module. Each of these components or subunits of the device will now be described in greater detail.

Thermal Chip Module

As summarized above, devices described herein include a thermal chip module. The devices may include a single thermal chip module, or two thermal chip modules. Thermal chip modules are plate or chip type structures that include one or more nodes, where each node is configured to accommodate a CLC on a surface of a carrier liquid positioned at the bottom of the node. Each node may be open at the top to provide for liquid access to a CLC present in the node. The volume defined by a given node of a thermal chip module may vary, and in some instances ranges from 2 µl to 1 ml, such as 5 µl to 20 µl. The cross-sectional shape of a given node may also vary, where cross-sectional shapes of interest include, but are not limited to, circular, rectangular (including square), triangular, etc. While the dimensions of each node may vary, in some instances the nodes have a longest cross-sectional dimension (e.g., diameter) ranging from 1 mm to 25 mm, such as 2.5 mm to 10 mm and a depth ranging from 1 mm to 20 mm, such as 3 to 10 mm. The number of nodes present in a given thermal chip module may also vary, ranging in some instances from 1 to 2000, such as 10 to 768. In some embodiments, the number of nodes is 96 or 384, e.g., in embodiments where correspondence with conventional multi-well plates is desired.

Thermal chip modules include, in some instances a node-defining base plate made of a convenient material and configured to define the nodes of the module. While the node-defining base plate may be made of any convenient material, in some instances the node-defining base plate is made of thermally conductive material. Materials of interest include, but are not limited to thermally conductive materials, e.g., composites, ceramics, and metals, including aluminum. While the dimensions of the node-defining plate may vary, in some instances the node-defining plate has a length ranging from 10 mm to 400 mm, such as 10 mm to 200 mm cm; a width ranging from 10 mm to 400 mm, such as 10 mm to 200 mm cm and a height ranging from 1 mm to 20 mm, such as 3 mm to 10 mm cm.

As mentioned above, each node defined by the node-defining plate is configured to accommodate a carrier liquid for a CLC at its bottom portion. While a given plate may have nodes with a closed bottom, such that during use an amount of carrier liquid is individually positioned at the bottom of each node, in some instances the chip module is configured such that the nodes are open at their bottom to provide for a common carrier liquid in each node. In some instances, the node-defining plate defining nodes with open bottoms is operably coupled to a base or vessel portion, sized and shaped to contain a bath of carrier liquid such that each node has the same level of carrier liquid present in its bottom portion. The carrier liquid may have a free surface on which CLCs may be accommodated. Like the node-defining plate, the vessel can be highly thermally conductive, e.g., composites, ceramics, and metals, in particular, aluminum, so that heat applied to the vessel will be spread evenly through the carrier liquid and into the CLCs.

An aspect of the thermal chip modules is that they are thermally controlled, such that the temperature of the environment defined by each node (and therefore experienced by a CLC accommodated therein) may be controlled, e.g., including precisely controlled, e.g., to a tenth of degree or better. The range of temperature control may vary, where in some instances the temperature may be controlled between 4 to 120° C., such as 4 to 98° C. To provide for thermal control, the thermal chip module may include heating and/or cooling elements. For example, the thermal chip module may include a cooling region configured to be operably attached to temperature modulator, e.g., a thermoelectric module, a fluidic cooling system or a forced convection cooling system. The chip module may also include a heating element in thermal contact with the vessel. The heating element could be, for example, an etched foil heater electrically connected to a controller, the controller being programmed to activate the heating element to generate a desired thermocycle in nodes and the CLCs accommodated therein. Alternatively, the heating element may be an electrical wire, activated by passing an electrical current through the wire. The wire may be electrically insulated with a material, for example, PTFE, that can also be used to form the stabilization features. In this embodiment, the heating element need not be in direct thermal contact with the vessel; the heat will be more directly transferred to the CLCs through the electrically insulating stabilization features. The stabilization features can be integral with the wire's insulation, and can be formed of the same material. Alternatively, the stabilization features can be attached to the wire, and/or made of a different material than the insulation. Such an embodiment may or may not also include nodes comprising the stabilization features. Stabilization features are further described in PCT application serial no. PCT/IB2014/001784 published as WO/2014/188281; the disclosure of which is herein incorporated by reference. Alternatively stabilization features may be present on only the module and not be integrated with the heating element. The heating element can be incorporated into the node-defining plate or vessel, or can be provided as a separate element of the module, e.g., as desired.

Figure 3:
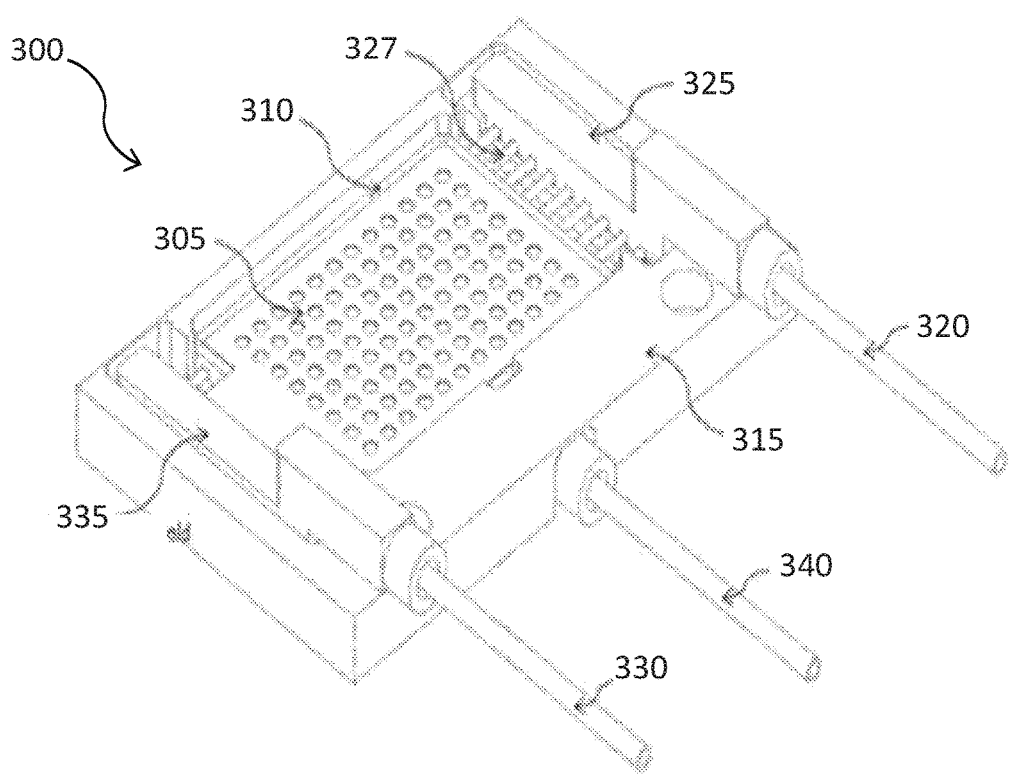
FIG. 3 provides a three-dimensional illustration of a thermal chip module.

One example of such a plate is schematically shown in FIG. 3. FIG. 3 provides a three-dimensional view of a 96 node thermal chip module, in accordance with an embodiment of the invention. Thermal chip module 300 includes 96 nodes 305. Each node 305 has a circular cross-sectional shape and is open both at the top and bottom, such that the nodes are cylinders. The nodes 305 are present in node-defining plate 310, which is made of a thermally conductive material, e.g., as described above. The module further includes a heater element 315 and fluidic cooling element made up of a coolant inlet 320 operatively coupled to a head inlet manifold 325 which in turn is operatively coupled to cooling tube array 327, and a coolant outlet 330 operatively coupled to header outlet manifold 335. Underneath the node-defining plate 310 is a common carrier liquid reservoir (not shown) which is fluidically coupled to a carrier liquid reservoir (not shown) by conduit 340. Other arrangements of the elements are possible as well. In some cases it may be beneficial to locate the heating element as close as possible to the stabilization features where the CLCs are typically located. Since it is the temperature of the samples within the CLCs that should be controlled, locating the heating element as close to the CLCs as possible can reduce energy consumption and increase efficiency, while also reducing evaporation of the carrier liquid.

The module can be configured to allow for through CLC optical interrogation, wherein a line of sight from a detector to a CLC is maintained through the plate. Optical detection methods include but are not limited to fluorescence, absorbance, Raman, interferometry and shadow-graphy.

The thermal chip module can also be operatively coupled to a lid sized and shaped to mate with the module or portion thereof, e.g., node-defining plate, so as to enclose the nodes and any CLCs accommodated therein. The lid may be openable and closeable by an automatic actuator, or may be manually operated. The lid can seal the carrier liquid into the vessel in order to inhibit evaporation of the carrier liquid. The lid can partially seal against the vessel, or it can be substantially airtight, maintaining a pressure seal. The lid can be transparent to any particularly desired wavelength of light, to allow for electromagnetic interrogation of the CLCs. A heating element can be included in the lid, as desired. The lid can be thermally controlled as desired, such that the temperature of the lid may be modulated to a desired value.

Level Control System

As described above, in some instances the thermal chip modules include a common vessel positioned beneath a node defining plate for providing a common carrier liquid in the bottom of each node of the node defining plate. In such embodiments, the device may include a level control system that is configured to maintain carrier liquid (e.g., oil) height within the thermal chip module(s) at a desired and determined level. The level control system is one that keeps the carrier liquid at the bottom of each node at a desired (and in some instances known) height above the bottom of the node. In some instances, the system is one that keeps the carrier liquid at the bottom of each node at the same level in each node, such that the carrier liquid level is uniform across all of the nodes of the thermal chip module or modules in the device. Maintaining the carrier liquid at a common, uniform level in the nodes maintains the CLCs in the nodes at a common position in the nodes, facilitating automated manipulation of CLCs in the nodes.

Figure 4:
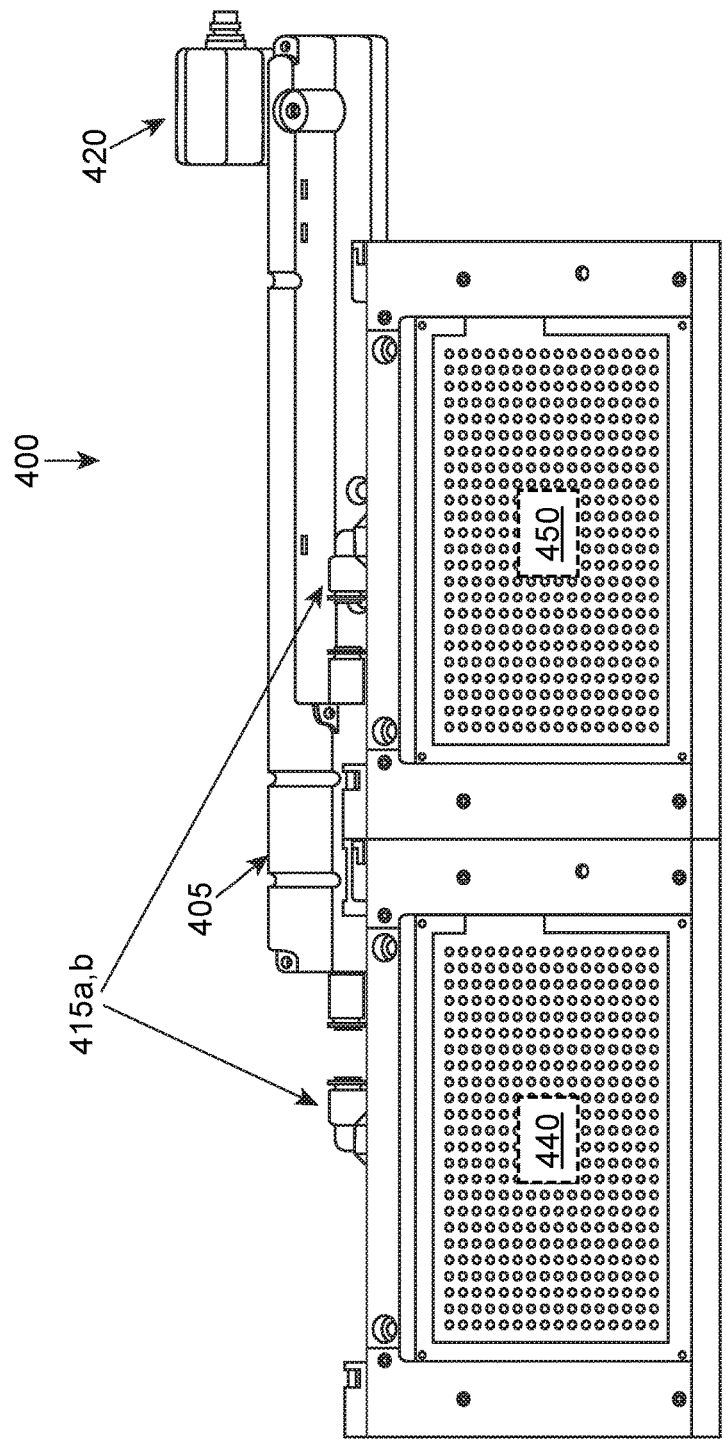
FIG. 4 provides a three-dimensional illustration of a level control system.

An embodiment of a level control system that finds use in device embodiments described herein that have two thermal chip modules is illustrated in FIG. 4. As shown in FIG. 4, level control system 400 includes a carrier liquid reservoir 405 common to both thermal chip modules 440 and 450 that is configured to be fluidically connected to each thermal chip module 440 and 450 by an outlet (410a, 410b) which couples to each thermal chip module's carrier liquid inlet (415a, 415b). The carrier liquid level in the reservoir 405 is monitored by a sensor 420, such as an ultrasonic sensor. By maintaining the carrier liquid level at the desired level in the reservoir 405, the liquid level is also maintained at the desired level in each of the nodes of the two thermal chip modules.

Figure 5:
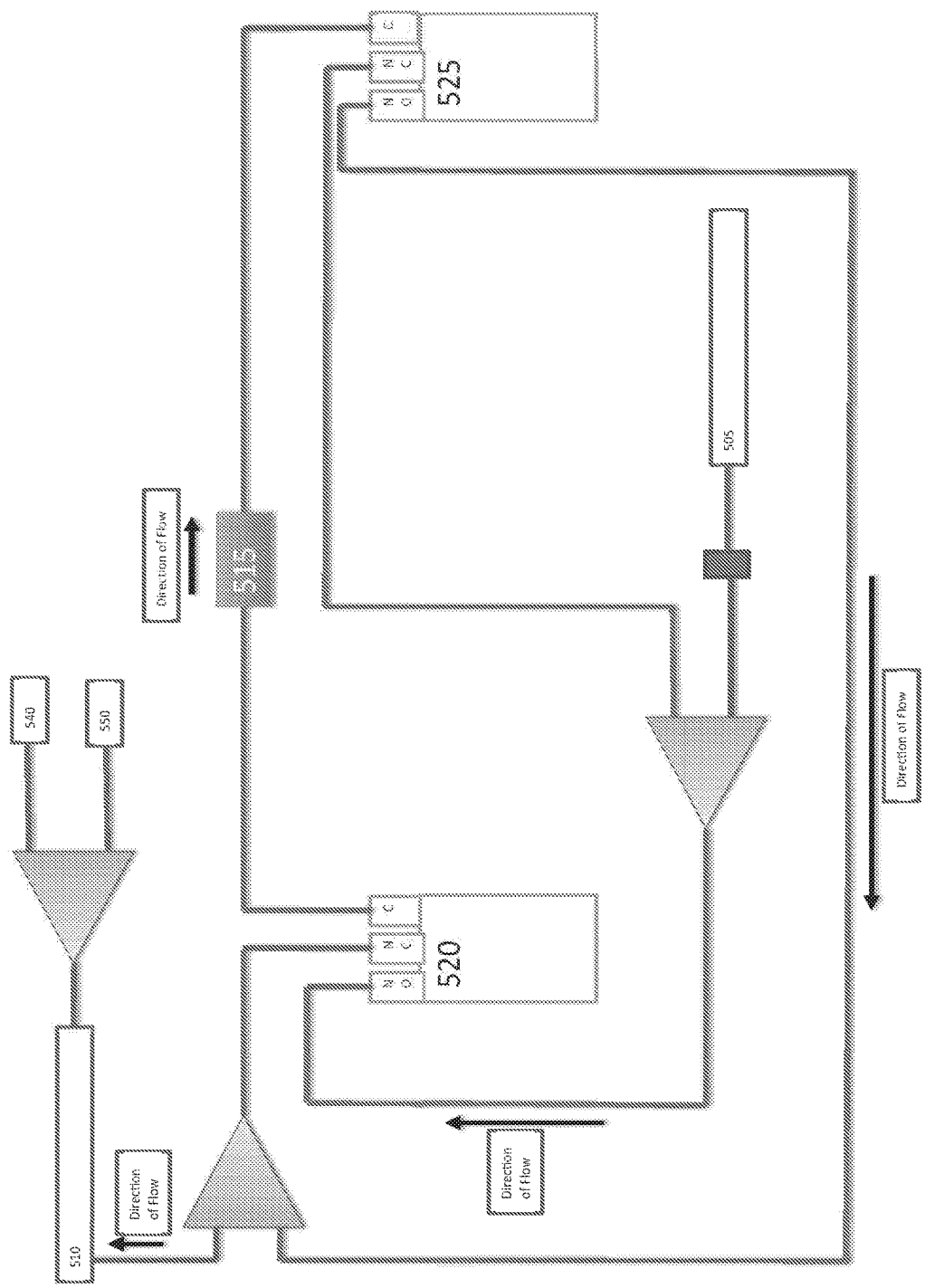
FIG. 5 provides a schematic diagram of the fluidics of a level control system such as that illustrated in FIG. 4.

The level control system depicted in FIG. 4 is configured to accurately maintain a desired level of carrier liquid in the common reservoir 405 and thereby accurately maintain a desired level of carrier liquid in each node of thermal chip modules 440 and 450. In one instance, the level control system includes a fluidic arrangement as depicted in FIG. 5. As illustrated in FIG. 5, a carrier liquid is pumped from the supply bottle 505 to a common reservoir 510 positioned beside the thermal chip modules 540 and 550, where the carrier liquid level is monitored by an ultrasonic sensor. The carrier liquid gravity feeds into the two thermal chip modules 540 and 550 from the common reservoir 510 and the reservoir 510 is filled or emptied to maintain the level at the set point within the set tolerance, thereby controlling the level in the bottom of each node of the thermal chip modules 540 and 550. The pump 515 has variable speed control which allows for quick priming of the system and reduced speed for smooth level control at the set point. In the embodiment shown in FIG. 5, the pump 515 is not reversible so two 3/2 solenoid valves 520 and 525 are used to reverse the flow from the reservoir 510 when the level needs to be lowered by pumping the carrier liquid back to the supply bottle 505.

Plate Locations

Figure 11:
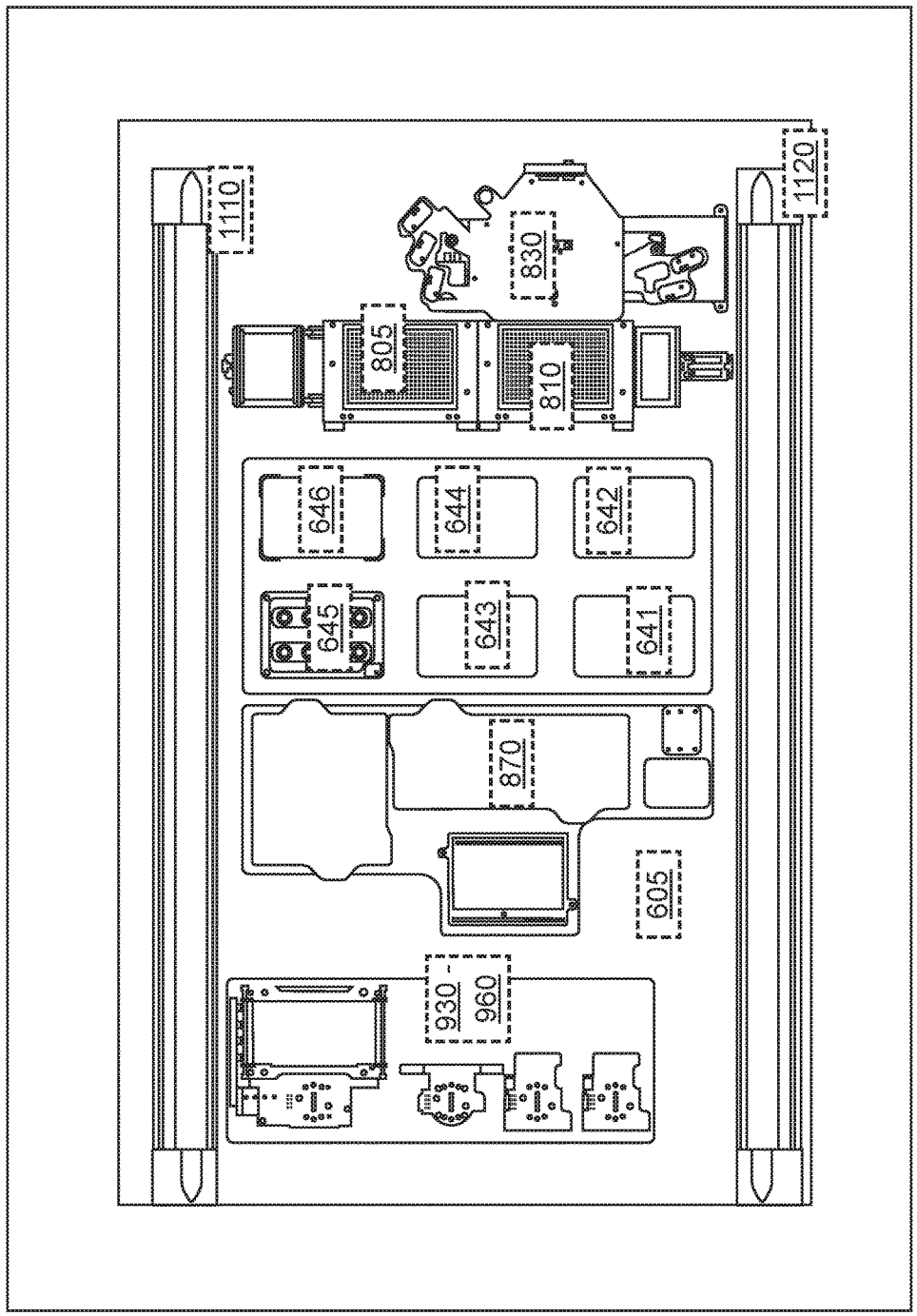
FIG. 11 provides an overhead view of the main deck of the device.

As summarized above, devices described herein include one or more plate locations. While the number of plate locations present in the device may vary, in some instances the device includes 1 to 10 plate locations, such as 2 to 8 plate locations, e.g., 6 plate locations. The plate location(s) may be arranged in any convenient manner in the device, where in some instances in which the device includes a plurality of plate locations, the plurality of plate locations are arranged adjacent to each other, e.g., in a portrait format relative to an entry port of the device, e.g., as shown in FIG. 11. Plate locations are regions or areas of the device configured to hold a laboratory plate, such as a multi-well plate, e.g., a 96 or 384 multi-well plate, or analogous structure, e.g., a test tube holder or rack, etc. A given plate location may be a simple stage or support configured to hold a laboratory plate. While the dimensions of the plate locations may vary, in some instances the plate locations will have a planar surface configured to stably associate with a laboratory plate, where the planar surface may have an area ranging from 10 mm to 400 mm, such as 10 mm to 200 mm. The planar surface may have any convenient shape, e.g., circular, rectangular (including square), triangular, oval, etc., as desired. To provide for stable association between a plate location and a research plate, the plate location may include one or more stable association elements, e.g., clips, alignment posts, etc.

In some instances, the plate location may be thermally modulated, by which is meant that the temperature of the plate location may be controllable, e.g., so as to control the temperature of a research plate (and the contents thereof) stably associated with the plate location. Any convenient temperature modulator may be employed to control the temperature of the plate location in a desired manner, where temperature modulators that may be employed include those described above in connection with the thermal chip module.

In some instances, a given plate location may be configured to be agitated, i.e., the plate location is a shaker unit. As such, it may include an agitator (e.g., vibrator or shaker component). While the frequency of the movement of the plate location provided by the agitator component may vary, in some instances that agitator may be configured to move the plate location between first and second positions at a frequency ranging from 1 rpm to 4000 rpm, such as 50 rpm to 2500 rpm, where the distance between the first and second positions may vary, and in some instances ranges from 10 mm to 400 mm, such as 25 mm to 100 mm.

As reviewed above, in some instances the device includes six different plate locations. While the six different plate locations may be employed for various purposes, in some embodiments the device includes two sample plate locations, which plate locations are configured to hold laboratory plates holding nucleic acid samples. In addition to the two sample plate locations, the device may include two barcode plate locations, which plate locations are configured to hold laboratory plates holding identifier nucleic acid reagent, e.g., barcode reagents, which in some instances may include sequencing adapter domains, as desired. In such devices, the shaker unit plate may be configured to hold a laboratory plate of magnetic beads, e.g., for use in a purification step, such as described in greater detail below. The final plate may be configured to hold one or more receptacles for receiving the final library product once produced.

Robotically Controlled Liquid Handler

As summarized above, devices described herein include a robotically controlled liquid handler. The robotically controlled liquid handler is a unit that is configured to transfer liquid and/or CLCs between various locations of the device, such as the plate location(s) and the thermal chip module. In a general sense, the robotic liquid handler may be any liquid handling unit that is capable of transferring a quantity of liquid between two distinct locations of the device, such as a plate location and a node of a thermal chip module. Robotic liquid handlers of interest are ones that can remove a defined volume of liquid from a first location of the device, such as a well of a laboratory plate or a node of a thermal chip module, and deposit that volume of liquid at second location of the device, e.g., a node of a thermal chip module or a product collection location. While the volume of liquid that the handler is configured to transfer may vary, in some instances the volume ranges from 100 nl to 10 ml, such as 100 nl to 1 ml.

The robotic liquid handler is, in some instances, a capillary system configured for dispensing an aqueous liquid. Such a capillary system can include a capillary tube having an inner surface that defines the capillary, or lumen. The tube can also have an outer surface. The outer surface may be generally cylindrical, including the side, top and bottom. The inner surface can include two regions, a distal metering region and a proximal limiting region. The metering region of the inner surface may be substantially hydrophilic while the limiting region of the inner surface may be substantially hydrophobic. The entire outer surface may also be hydrophobic.

When an end, herein labelled the distal end, of the capillary tube is brought into contact with an aqueous sample, the sample is drawn by capillary action into the lumen. But the capillary action will only work to the extent that the aqueous sample is contained within a hydrophilic, i.e., wettable, section of the lumen. When enough aqueous sample has been drawn into the lumen that the metering region is entirely filled, capillary action will cease to draw in additional sample liquid, because no further wettable surface is available to the aqueous sample. In this way, the capillary action can be exploited to precisely meter a desired quantity of aqueous liquid. For a lumen of constant cross-sectional area, the volume of liquid drawn in by capillary action will be equal to the length of the metering section times the cross-sectional area of the lumen.

In some embodiments, the metering region and limiting region can be constructed as follows. A length of capillary tubing can be coated with, or formed entirely from, a hydrophobic polymer, for example a fluorocarbon polymer such as polytetrafluoroethylene (PTFE). An etching solution is then passed through the interior lumen of the tube, stripping the PTFE coating of fluorine atoms near the surface of the PTFE. Fluorine atoms are typically stripped down to a depth a few Angstroms by this process. The resulting etched PTFE surface is hydrophilic. The tube is then cleaned and cut to length to form a metering region having a desired internal volume. That internally etched, internally hydrophilic section of tubing is then attached to a section of hydrophobic tubing to form the entire capillary tube. In some embodiments polymers, such as polyimide, can be used to form the capillary tube.

In some embodiments, the capillary tube is formed of a glass substrate. Glass is naturally hydrophilic, so where the substrate is glass, instead of, for example, a naturally hydrophobic polymer, no surface treatment is necessary to form the metering region. The outer surface and limiting region may be formed by coating the glass with a hydrophobic material, such as the polymers mentioned above.

One benefit of making the outer surface of the tube, especially the distal end of the tube, hydrophobic is that the aqueous sample will not cling to such material. Thus the hydrophobic outer surface protects the system from contaminating one aqueous liquid sample with droplets from a different aqueous sample. Inserting the distal end of the tube into an aqueous sample will results in liquid drawn into the hydrophilic metering region, but not clinging to the hydrophobic region.

In addition to a capillary tube, a capillary system can also include a pressure source in fluid communication with the proximal end of the tube. The pressure source can provide positive pressure from any convenient gas, e.g., air. Application of the positive pressure can be used to drive an aqueous sample out of the capillary. The lowest positive air pressure is found at which the aqueous sample is completely driven out of the capillary and thereafter may be accurately and precisely controlled. The positive pressure may be evenly distributed when there are multiple capillaries used in parallel. The shortest time is found for the positive pressure to be applied to the capillary to allow all of the aqueous sample to be driven out and the pressure neutralized immediately to prevent air being blown out through the capillary once the aqueous has been driven out of the capillary. The positive pressure and time applied may then be used to carry out sample dispense testing where the sample volume accuracy and precision, sample breakup and disturbance to the CLC are investigated. The positive pressure and time are then adjusted to obtain the optimum sample dispense to CLC within these parameters. The system can also include a capillary controller programmed to apply the positive pressure at a desired time so that the aqueous sample is dispensed at a predetermined location. The location could be, for example, a stabilization site for a composite liquid cell, where an aliquot of encapsulating fluid could be ready to receive the aqueous sample. It should be noted that, while positive pressure can be used to drive the aqueous liquid out of the lumen, no negative pressure is needed to draw the liquid into the lumen because the liquid is drawn in by capillary action.

The capillary system can also include an air sheath, which includes an externally applied air flow to the capillary tube. The externally applied air flow reduces the likelihood that an aqueous sample will attach to any external hydrophilic region.

The capillary system can also include an actuator to move the capillary tube between locations. The actuator can be controlled by the capillary controller, which can be programmed to cause the actuator to move the tube. A typical program might first move the distal end of the tube into contact with an aqueous sample so as to draw the aqueous sample into the tube, then move the capillary tube so that the distal end is adjacent to a dispensing location such as a stabilizing feature or an existing composite liquid cell (hereinafter "CLC"), and finally apply sufficient positive pressure to the proximal end of the tube to eject the aqueous sample from the distal end of the tube.

While the dimensions of the capillary tube may vary, in one embodiment, the internal diameter of the capillary tube is about 200 to 250 µm, such as 221 or 230 µm, and the outer diameter is about 800 µm. Any volume of aqueous solution can be chosen to be drawn into the system. Particular capillary tubes may be designed to draw in from about 10 nanoliters to about 10000 nanoliters, such as 500 nanoliters.

In another embodiment, for multiple capillary metering from a single controller-multiple capillary tubes with the inner surface having a single distal metering region are arranged within a cavity, thereby providing a limiting region.

In another embodiment the pressure controller variably controls the capillary metering volume. The treated tube is cut to a given length and based on the radius of that tube this then gives a set maximum volume. The volume within distal metering region is controlled using air pressure within the assembly. The air pressure is used to dispense however in this embodiment a controlled constant pressure is maintained within the capillary tube—thereby providing a volume control within the hydrophilic distal metering region. This is achieved by balancing the pressure force against the capillary force for a given volume. The fluid will capillary to a height that is matched by pressure force. Change the pressure and the volume is changed. This is all within the total capillary height for a given fluid and tube radius.

In another embodiment, a capillary metering system can include a plurality of capillary tubes. The proximal ends of all the capillaries can be in fluid communication with a single pressure conduit, and the pressure conduit in fluid communication with the pressure source. In this way, a single pressure source can be used to apply a single positive pressure to simultaneously dispense liquid from all of the plurality of capillary tubes. Similarly, a single pressure source can apply a single positive pressure to balance the capillary force in all of the plurality of capillary tubes. In such embodiments, the plurality of capillary tubes may be present in a head subunit which includes a holder for the plurality of capillary tubes. The number of capillary tubes in a head subunit may vary, where in some instances the number ranges from 12 to 768, such as 24 to 384, e.g., 24 to 96, including 24 to 48. The capillary tubes may be arranged in the head subunit so that tubes readily align with wells of a laboratory plate when the head is positioned over a laboratory plate, e.g., one that is present on a plate location of the device.

Further details regarding capillary liquid handling systems that may be employed in the device are provided in PCT application Serial No. PCT/IB2013/003145 published as WO 2014/08345; the disclosure of which is herein incorporated by reference.

Of interest are robotic liquid handling systems that are further configured for making and processing CLCs, e.g., in CLC mediated NGS library production protocols. In such embodiments, the liquid handling system may include a CLC forming component like the one described in detail in U.S. Pat. No. 8,465,707, the disclosure of which is herein incorporated by reference. As described, a CLC-forming system can include a sample-liquid input, an encapsulating-liquid input, a liquid-handling system, and a cell-forming controller operably connected to the liquid-handling system. The cell-forming controller can be programmed to cause the liquid handling system to (1) draw an encapsulating liquid from the encapsulating-liquid input, (2) discharge the drawn encapsulating liquid (a) onto a free surface of a carrier liquid at the bottom of a node of a thermal chip module, the encapsulating liquid being immiscible with the carrier liquid, so that the discharged encapsulating liquid does not mix with the carrier liquid, but instead floats on top of the carrier liquid, (3) draw a sample liquid from well of a research plate positioned at a plate location, and (4) discharge the drawn sample liquid into the node in a non-contact manner (the sample liquid being immiscible with the encapsulating liquid and with the carrier liquid) such that the sample liquid does not mix with the encapsulating liquid or with the carrier liquid. In such a system, the capillary system and reusable plate can be located relative to one another so that the actuator is capable of moving the capillary tube to a dispensing location of the node. This will allow the capillary tube to dispense, for example, a reagent into an existing CLC, or to deposit sample material, e.g., at a stabilization feature of the node, to create a CLC. Relatedly, the capillary system could simultaneously be the liquid handling system of the CLC-forming system. Likewise, the cell-forming controller and the capillary controller can be a single controller.

In some instances, the robotic liquid handler includes a mover that can be selectively operatively coupled to a plurality of distinct interchangeable liquid manipulator heads, e.g., capillary heads such as described above. In such embodiments, the mover can be coupled and decoupled to a liquid manipulator head from a collection of two or more liquid manipulator heads, such that the liquid manipulator heads are interchangeable (i.e., can be substituted for one another) with the mover. Where mover provides for negative pressure to the liquid manipulator head when in use, the coupling configuration provides for negative pressure to be coupled to the liquid manipulators, e.g., capillaries, of the head when coupled to the mover. The number of interchangeable liquid manipulator heads in the device may vary, ranging in some instances from 2 to 6, such as 2 to 4. The function of such interchangeable liquid manipulator heads may also vary, where in some instances the device includes interchangeable liquid manipulator heads configured for sample dispense, barcode dispense, reagent dispense, vacuum and purification tasks. The mover to which the interchangeable heads may be operatively coupled is a subunit of the device that is configured to move an interchangeable head between two or more locations of the device. The mover may be a robotic arm or other convenient structure that is configured to move a given interchangeable head in the X and/or Y and/or Z direction in the device.

Bulk Reagent Dispenser

As summarized above, devices described herein include a bulk reagent dispenser. The bulk reagent dispenser is an automated reagent dispenser that is configured to deposit a metered volume of a reagent composition, e.g., a liquid reagent composition, into the nodes of the thermal chip module. In some instances, the bulk reagent dispenser is configured to deposit a metered volume of a reagent composition, e.g., polymerase, nucleotide mix, primer, adapter, buffer, ligase etc., into each node of a thermal chip module, such that it can access each node of the thermal chip module, e.g., by individually introducing a reagent dispenser, such as a liquid reagent dispenser, into the different nodes of a thermal chip module. In some instances, the bulk reagent dispenser includes a reagent metering element (such as a liquid reagent metering unit) operatively coupled to a bulk reagent source (such as a liquid reagent reservoir, e.g., present in a cartridge) by an automated movement arm, e.g., an arm that is configured to move in the X and/or Y and/or Z directions. In some instances, the bulk reagent dispenser is configured to be able to individually introduce a metered amount of a reagent composition into a node and any CLC present therein in a non-contact microfluidic dispensing manner, e.g., by dropping an amount of the reagent composition onto a CLC in the node such that the reagent composition merges with the CLC in the node.

Fluidics Module

Devices described herein may include a fluidics module that includes one or more liquid reservoirs, e.g., for system fluids, waste collection, etc. System fluids of interest include, but are not limited to, wash fluids, elution fluids, etc. Where desired, the waste collection reservoir is operatively coupled to a single waste drain.

Additional Aspects

Devices described herein may be configured to automatically produce large numbers of libraries in a short period of time following commencement of a given library preparation run. The numbers of library samples that the devices may be configured to simultaneously produce ranges in some instances from 1 to 1000, such as 8 to 768, e.g., 96, 192, 384 or 768 libraries. While the amount of time required to produce such libraries may vary, in some instances the amount of time ranges from 1 hour to 48 hours, such as 2 to 36 hours, e.g., 6 hours.

To facilitate reagent handling and device set up, the device may include a control processor in operative communication with a handheld unique identifier (e.g., barcode) scanner, which scanner may communicate with the processor via a wired or wireless communication protocol. Such embodiments may be used to upload identifying information regarding laboratory plates and/or reagent sources into the control processor of the device in order configure the device to automatically perform a library preparation protocol.

Specific Embodiment

Figure 6:
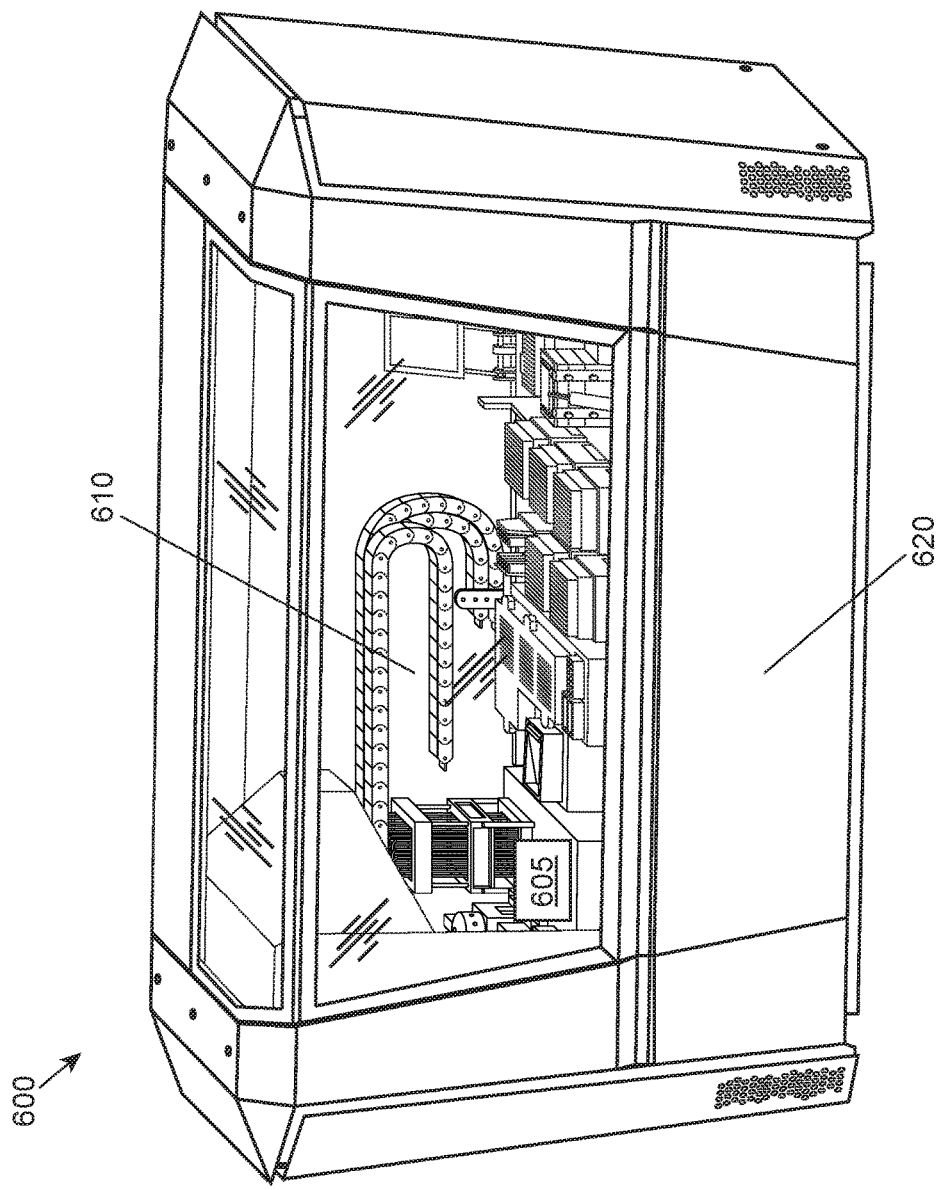
FIG. 6 provides a three-dimensional illustration of a closed NGS library preparation device.

A specific embodiment of a library preparation device according to the invention is depicted in FIGS. 6 to 11. FIG. 6 provides an overall view of the device 600. Device 600 is compact, at about 0.805 m deep, 1.54 m long, and 0.885 m high, and weighs less 500 kg or less, such as 300 kg or less, including 180 kg or less. The system is designed to be controlled via a user interface on a typical Windows personal computer on an adjacent bench top. The device shown in FIG. 6 is configured to create DNA libraries using a composite liquid cell (CLC) mediated protocol. The device is configured to create 768 libraries in about 6 hours using CLCs; operate with a minimum sample census of 24 samples; deliver sample and barcode in multiples of 24; and for lower numbers be able to use a substitute buffer to ensure the efficient operation of the system.

Figure 7:
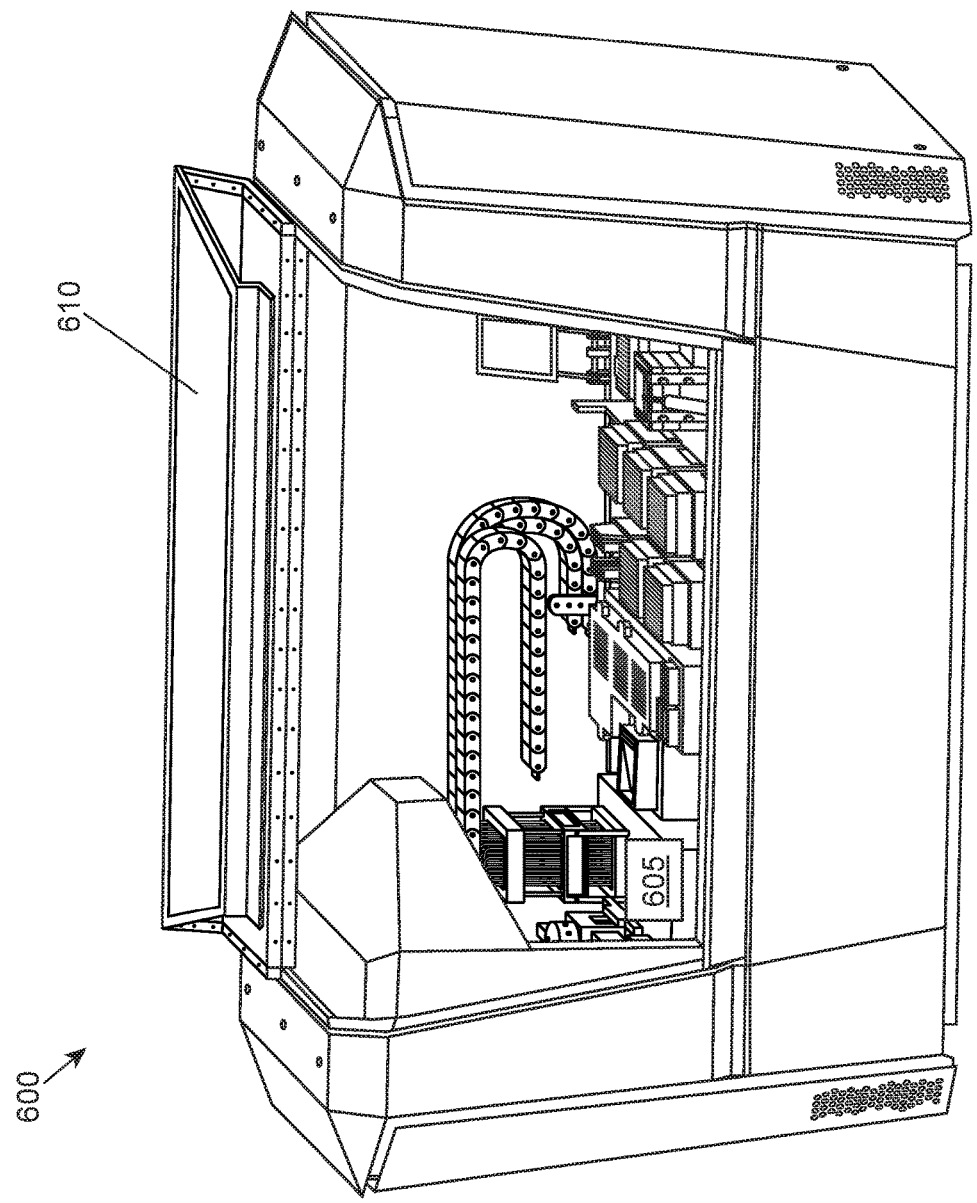
FIG. 7 provides a three-dimensional illustration of an open NGS library preparation device showing the main deck.

As shown in FIG. 6, the device 600 includes a main deck 605 where the processing steps are performed, which main deck is accessible via an access door 610. User access to the main deck is accomplished via a user operated hood (access door 610) which is interlocked. The device 600 also includes a services deck (not shown) situated beneath the main deck 605 where peripheral hardware is located and which is accessible via a services drawer 620. Access door 610 is clear or transparent to allow for viewing of the interior of the device and main deck 605 thereof during use with the door is closed. FIG. 7 provides a view of device 600 with door 610 in the open position, allowing access to the main deck 605. The system enclosure has active internal-external air exchange.

Figure 8:
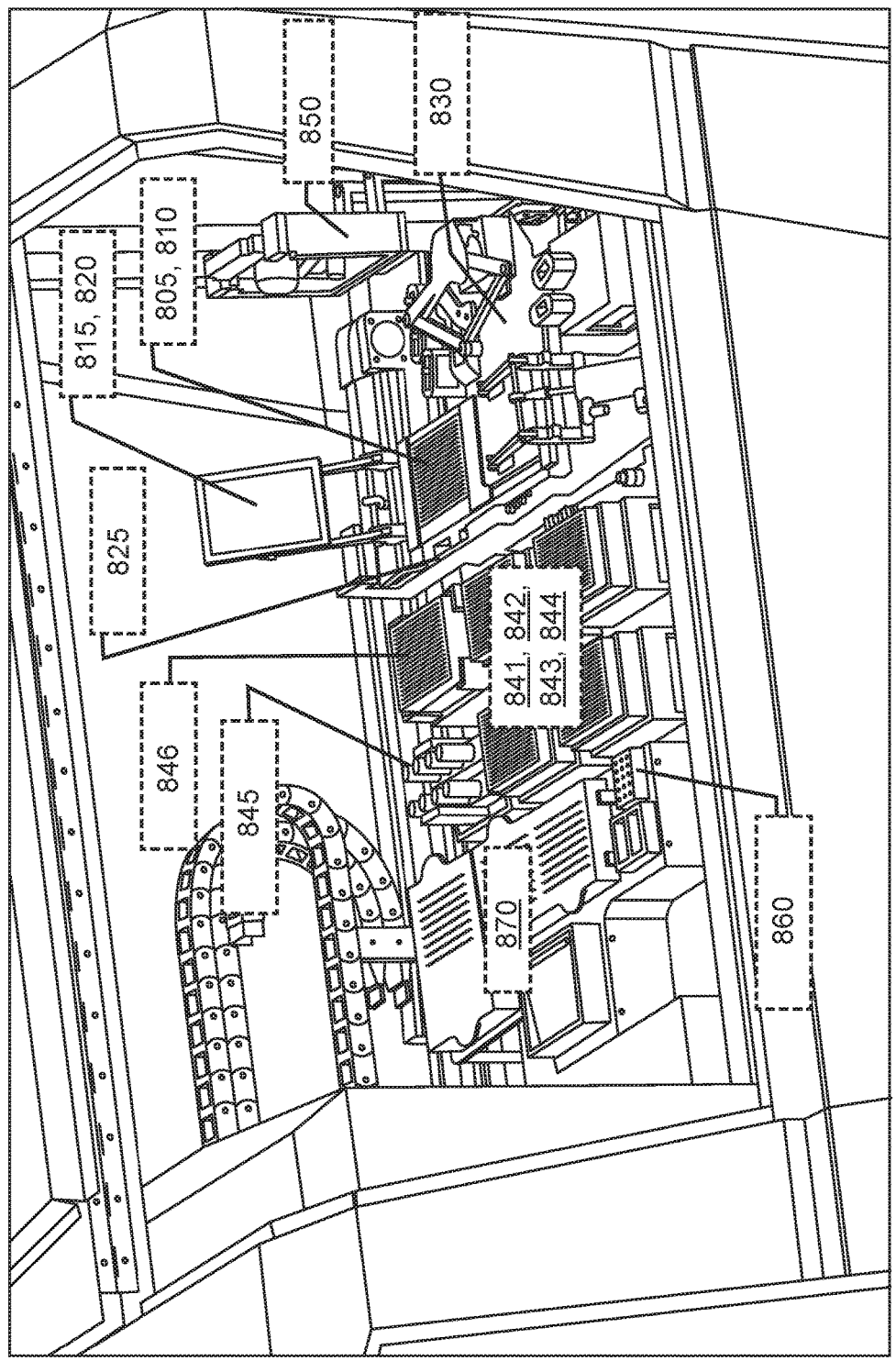
FIG. 8 provides a three-dimensional illustration of various components that are present on the main deck.

FIG. 8 provides a detailed view of the main deck 605 and components of the device located thereon. As shown in FIG. 8, present on main deck 605 are the following sub-components: (a) two independently controlled 384 node thermal chip modules 805 and 810, where the design of each module is based on the SBS format for a 384 well microtitre plate; (b) two mechanically actuated lids 815 and 820, one for each 384 thermal chip module (where each lid is thermally controlled and pneumatically actuated); (c) a level control system 825 such as described above which is configured to maintain the carrier oil height within the nodes of the thermal chip modules 805 and 810; (d) a single bulk reagent dispenser 830 capable of (i.e., configured for) accessing all nodes of each of the thermal chip modules, 805 and 810; and (d) six thermally controlled plate locations 841 to 846.

Bulk reagent dispenser 830 is configured to access all nodes of each 384 thermal chip module 805, 810 and dispense various reagents, such as a nucleotide mix (e.g., Mastermix from GenCell Biosystems), primer collection (e.g., a primer pool, which pool may or may not incorporate adapter sequences), enzymes, e.g., polymerase, FuPa, ligase, and other molecular reagents at the appropriate points within the protocol, described in greater detail below. The bulk reagent dispenser 830 is designed to accommodate one or more barcoded 'reagent cartridges' 850 which are loaded onto the dispensing unit. The bulk reagent dispenser is configured to accommodate a separately barcoded 'wash cartridge' which is interchanged with the 'reagent cartridge' when appropriate during a given protocol. The cartridges are compatible with standard laboratory tubes. Cartridge barcodes have separate codes to identify between reagent cartridges and wash cartridges. The design of the reagent cartridge is such that the reagent locations on the cartridge can be color coded and/or numbered to match corresponding micro-centrifuge tubes. The cartridge has locating features to ensure correct loading onto the dispensing unit.

As mentioned above, the device includes 6 plate locations: two of which (841, 842) are sample source locations, two of which (843, 844) are barcode source locations, one of which (845) is configured to receive library product (i.e., holds product receptacles) and one of which (846) is a shaker unit (While the device shown in FIG. 6 has this plate layout configuration, other configurations are also encompassed in the invention, e.g., 3 sample plates, 1 barcode plate, 1 shaker unit and 1 receptacle plate, etc.) Sample plates 841 and 842, Bead/Elution plate 846, barcode (i.e., index) plates 843 and 844 and library collection plate 846 are compatible with standard laboratory plates. An optional collection container for sample collection vessels may employ standard laboratory 5 ml tubes. Source plates for DNA, Barcode (i.e., Index), Beads and Elution buffer may be mounted on thermally controlled plate location units. As shown there is a capacity for ×4 source plates, ×1 shaker plate, ×1 library collection plate/vessels. The thermally controlled plate locations may have interchangeable adapters to facilitate alternative plate layouts on the main deck. Source plates may be orientated in the portrait view, e.g., as shown in FIG. 11. Source plates may be loaded with the A1 well in the bottom left corner as viewed in FIG. 11. Source plates may be either 1D and/or 2D barcoded and may be manually scanned by the user during run setup when prompted by the system software. Plate locations may be color coded to aid user loading. In some instances, a user is required to scan source plates, dispensing cartridges, pooling collection vessel during setup. For inputting run details manually, a blank template may be used with auto-fill options to populate information quickly for later editing.

Also shown is a capillary vacuum drying unit 860 accessible by interchangeable heads (not shown).

Wash station 870 is also shown, which includes wash solution reservoirs, whereby the fluid is pumped to each reservoir from separately located bottles and a small wash solution reservoir which is filled and replaced by the user. The system further includes a waste drain where all fluid waste is pumped to a separately located reservoir bottle. Wash troughs containing wash liquids may be accessible by the appropriate heads from the main deck 605. Wash troughs may be fed automatically from a separately located bottle. Wash bottles may hold sufficient fluid for one run on the system. Wash bottles may be color coded to aid user loading and avoid error.

Figure 9:
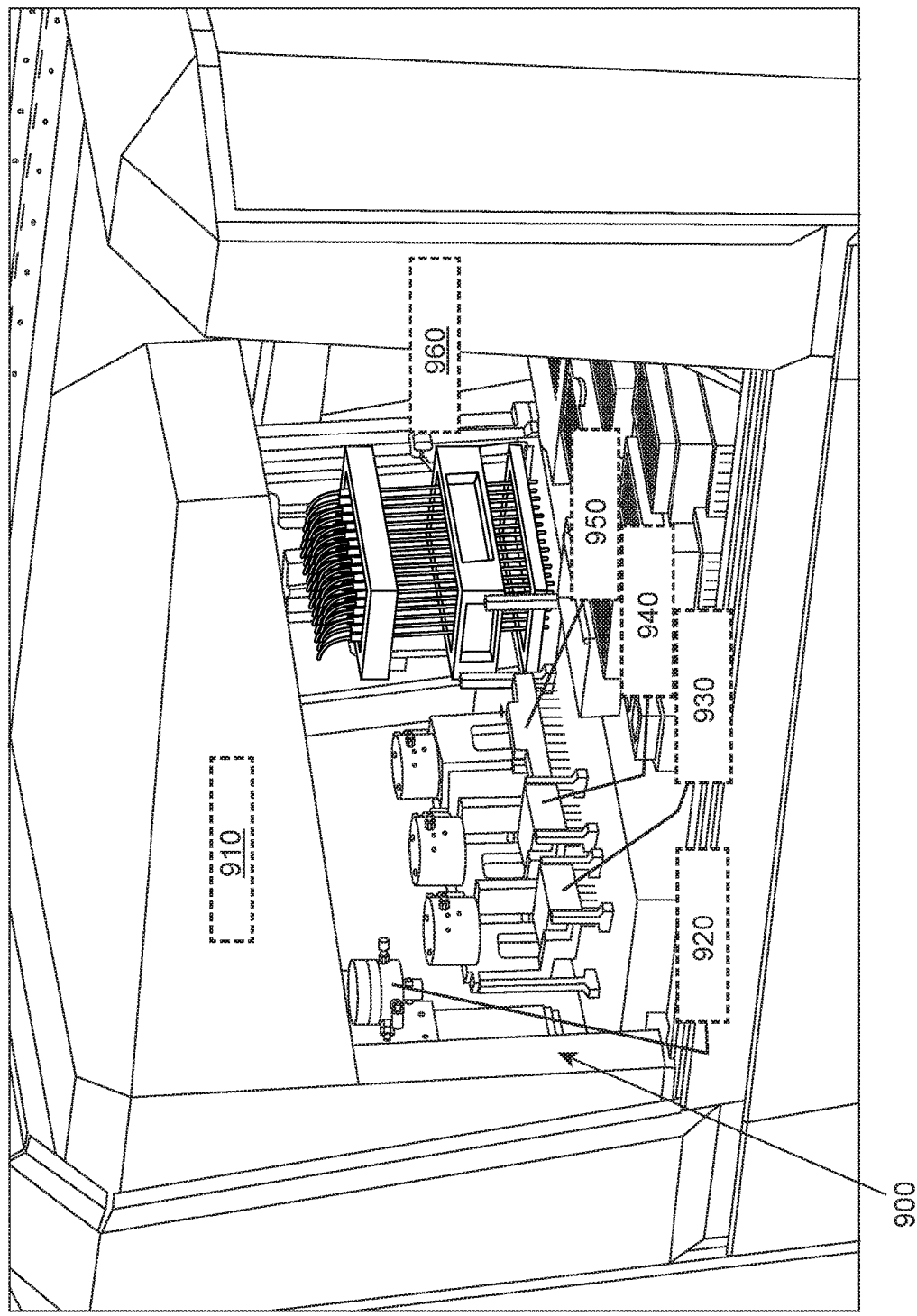
FIG. 9 provides a three-dimensional illustration of the robotic liquid hander and components thereof.

FIG. 9 provides a detailed view of the liquid handler component of the device. As shown in FIG. 9, robotically and pneumatically controlled liquid handler 900 includes a gantry 910 that is configured to be reversibly operably connected, i.e., engaged to and disengaged from, multiple distinct liquid handling heads and move such heads between different locations of the device. While the heads are described below in connection with a particular type of liquid transfer, e.g., sample or barcode, their function is not limited, since the heads are interchangeable and may be employed for any liquid transfer within the device, as desired. Specifically, liquid handler 900 includes a robotic change tool 920 which is configured to operably and reversibly engage the gantry 910 to each of: (a) a sample capillary metering head 930 for sample dispense (which is configured to transfer volumes of sample from wells in a laboratory plate on a plate location to nodes of a thermal chip module and deposit such into a CLC via a non-contact protocol); (b) a barcode capillary metering head 940 for barcode dispense (which is configured to transfer volumes of barcode reagent liquid from wells in a laboratory plate on a plate location to nodes of a thermal chip module and deposit such into a CLC via a non-contact protocol); (c) a vacuum head 950 (which may be used for a variety of purposes, e.g., to remove unwanted items form the nodes, at the end of each run to remove any encapsulate oil or aqueous remaining in the nodes of the thermal chip, in the thermal chip reset where a clean procedure can be run and the vacuum removes any wash buffers to waste); and (d) a purification head 960 for CLC laydown, purification, wash and pooling tasks (which is configured to obtain magnetic beads from the shaker unit; dispense the beads into nodes of the thermal chip module; retrieve beads with nucleic acid product bound thereto from the nodes and purify the nucleic acid product on the beads).

Figure 10:
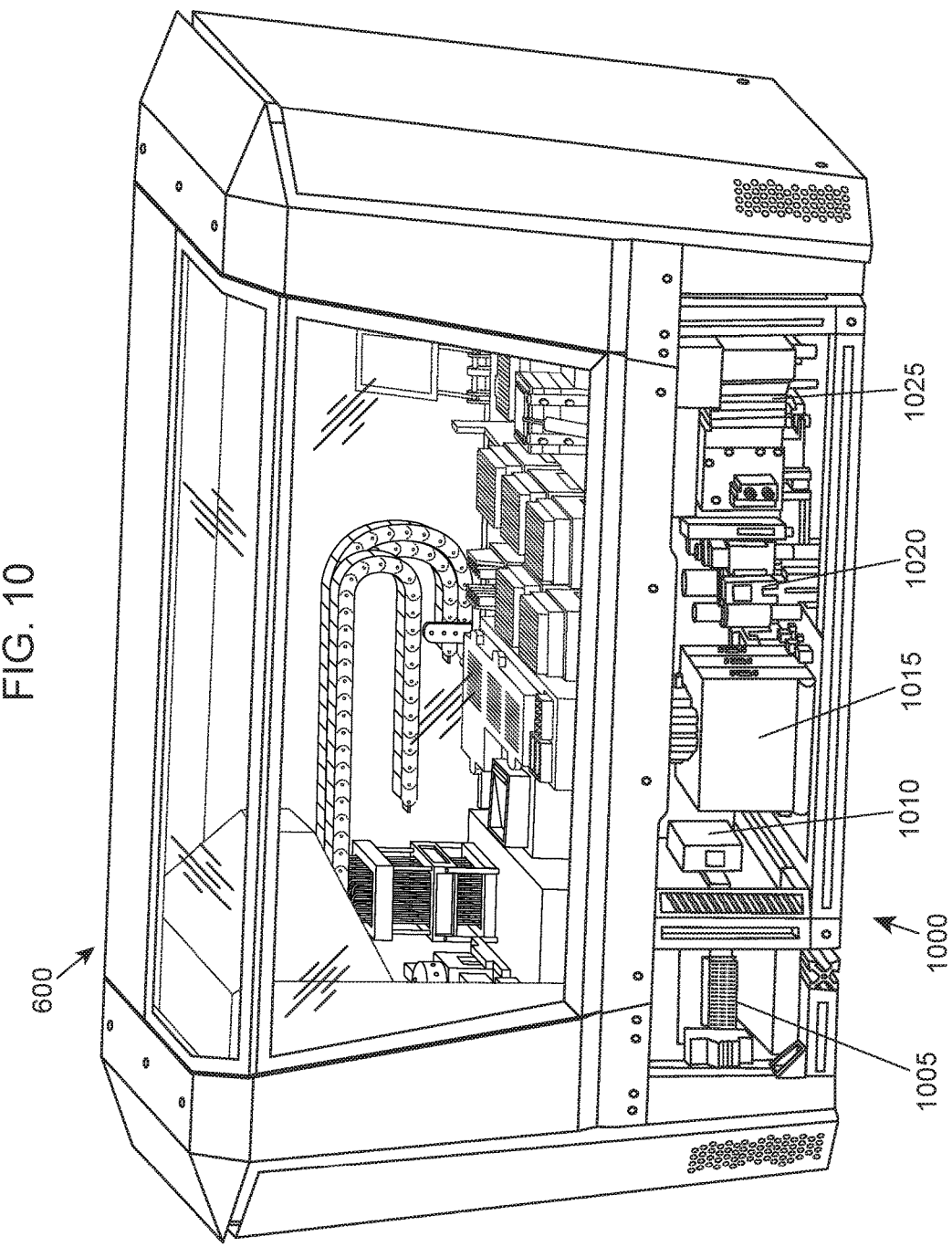
FIG. 10 provides a three-dimensional illustration of the services deck of the device.

FIG. 10 provides a view of the services deck 1000 of device 600, which is accessible via services door 620. As shown in FIG. 10, services deck 1000 includes an AC panel 1005, a DC panel 1010; a robotics motor controllers 1015; and air preparation module 1020 and a pneumatic controller 1025. The services deck 1000 is mounted on a moveable drawer for troubleshooting and preventative maintenance access, and moves outward from the front of the system.

FIG. 11 provides a top view of the main deck 605 of device 600, showing the layout of the different components on the main deck 605. As shown in FIG. 11, main deck 605 includes 6 plate locations, i.e., two sample plate locations (641 and 642); two barcode plate locations (643 and 644); a library collection plate 644 and a magnetic bead/shaker unit plat 645. Also shown are two thermal chip modules (805, 810); bulk reagent dispenser 830, wash station 870 and interchangeable heads 920 to 960 of liquid handler 900. Rails 1110 and 1120 are configured to provide for movement of liquid handler gantry 910 in the X direction across the main deck 605.

Device 600 further includes a handheld barcode scanner (not shown) configured to perform run setup and information tracking. Device 600 further includes an externally located fluidics module (not shown) which houses the reservoir bottles which supply system fluids; the CLC encapsulant oil, the CLC carrier oil, and wash liquids. Placeholders may be color coded or numbered to aid user setup and avoid errors. Bottle reservoirs may have quick-connect connections. Bottles may at minimum contain sufficient volume to complete a single system run.

Methods of NGS Library Preparation

Aspects of the invention include methods of producing a next generation sequencing (NGS) library from an initial nucleic acid sample by using a device of the invention, e.g., as described above, in a CLC mediated library preparation protocol. The devices of the invention may be employed to produce NGS libraries suitable for sequencing in a variety of different NGS platforms, including but not limited to: the HiSeq™, MiSeq™ and Genome Analyzer™ sequencing systems from Illumina®; the Ion PGM™ and Ion Proton™ sequencing systems from Ion Torrent™; the PACBIO RS II sequencing system from Pacific Biosciences, the SOLiD sequencing systems from Life Technologies™, the 454 GS FLX+ and GS Junior sequencing systems from Roche, or any other sequencing platform of interest.

In preparing an NGS library, a nucleic acid sample from which the library is to be prepared is first provided. Any convenient nucleic acid sample preparation method may be employed. Nucleic acid sample preparation may include fragmenting an initial nucleic acid source sample to produce a fragmented nucleic acid sample made up of nucleic acid fragments of suitable size for sequencing with a given NGS sequencing platform. Source nucleic acids of interest include, but are not limited to: deoxyribonucleic acids, e.g., genomic DNA, complementary DNA (or "cDNA", synthesized from any RNA or DNA of interest), recombinant DNA (e.g., plasmid DNA); ribonucleic acids, e.g., messenger RNA (mRNA), a microRNA (miRNA), a small interfering RNA (siRNA), a transacting small interfering RNA (ta-siRNA), a natural small interfering RNA (nat-siRNA), a ribosomal RNA (rRNA), a transfer RNA (tRNA), a small nucleolar RNA (snoRNA), a small nuclear RNA (snRNA), a long non-coding RNA (lncRNA), a non-coding RNA (ncRNA), a transfer-messenger RNA (tmRNA), a precursor messenger RNA (pre-mRNA), a small Cajal body-specific RNA (scaRNA), a piwi-interacting RNA (piRNA), an endoribonuclease-prepared siRNA (esiRNA), a small temporal RNA (stRNA), a signal recognition RNA, a telomere RNA, a ribozyme; etc.

Source nucleic acids may be fragmented using any convenient protocol, e.g., passing the sample one or more times through a micropipette tip or fine-gauge needle, nebulizing the sample, sonicating the sample (e.g., using a focused-ultrasonicator by Covaris, Inc. (Woburn, Mass.)), bead-mediated shearing, enzymatic shearing (e.g., using one or more RNA-shearing enzymes), chemical based fragmentation, e.g., using divalent cations, fragmentation buffer (which may be used in combination with heat) or any other suitable approach for shearing/fragmenting an initial nucleic acid to generate a shorter template nucleic acids suitable for NGS library preparation. In certain aspects, the template nucleic acids generated by shearing/fragmentation of a starting nucleic acid sample has a length of from 10 to 20 nucleotides, from 20 to 30 nucleotides, from 30 to 40 nucleotides, from 40 to 50 nucleotides, from 50 to 60 nucleotides, from 60 to 70 nucleotides, from 70 to 80 nucleotides, from 80 to 90 nucleotides, from 90 to 100 nucleotides, from 100 to 150 nucleotides, from 150 to 200, from 200 to 250 nucleotides in length, or from 200 to 1000 nucleotides or even from 1000 to 10,000 nucleotides, for example, as appropriate for the sequencing platform chosen.

Once prepared, the nucleic acid sample, along with any other samples from which an NGS library is to be prepared in a given run of the device, is placed into a well or analogous container of a sample plate and positioned on a sample plate location of the device, e.g., through an open access door to the main deck of the device. The device is also loaded with one or more laboratory plates comprising sample identifying nucleic acids (i.e., barcodes), purification magnetic beads, library product receptacles (e.g., configured to either maintain individual product libraries or pool two or more different product libraries), bulk reagent liquids, wash and purification fluids, CLC liquids, etc. In addition, the control instructions and data about a given run may be input into the device, e.g., by using an automated protocol (such as with a hand held barcode scanner) or manually via an appropriate user interface, etc. Control instructions may include the number of samples to be run, which may be input using any convenient protocol, e.g., via manually entered user data or a previously generated .csv file. Information to be input may further include the number of samples and location of samples. The device may include a main user interface. Where desired, the main user interface provides feedback for the following run status information: an animated graphical representation of the main deck showing current action being performed by the liquid handler; a status indicator for each chip indicating its progress through the overall protocol; a countdown timer to the completion of the total run, accurate to +/−10 min; a feedback panel for each chip which will show information pertaining to the current task being performed, i.e., thermal information, mantis dispense operation, and carrier oil level status; a warnings and errors panel where any issues flagged by software will be displayed. The device may further include a web services component, e.g., which is configured to monitor status and generate an email to be sent in the event of a critical error. The system may also be configured to produce an output file: e.g., which may include a barcoding file, and a plate definition file, where such files can be optionally amalgamated into one. The name of the run log folder may be included in the output file as well as the protocol that was run. Run logs may be numbered to keep them in order. The device may be configured to guide a user during setup. For example, during run setup a user may be guided through the cartridge loading sequence and prompted to scan the cartridge barcode when appropriate. The system's software may include a specific simple and integrated sub-program for bulk dispensing chip alignment. When a user is required to enter information, the system may prompt a user to select from a number of predefined options within a drop-down list rather than freely entering information. Following device set up, including closure of any open access door or other open component, the device is ready to perform an automated CLC mediated library preparation protocol.

As such, once the device is loaded with nucleic acid sample(s) and configured for a given NGS library production run, the run is started. During the run, the device first produces CLCs in the nodes of the thermal chip module(s), e.g., by placing suitable volumes of encapsulating liquid in the nodes of the thermal chip module(s) using the purification head of the robotic liquid handler. Next, the sample transfer head of the robotic liquid handler is exchanged for the purification head, and the sample transfer head is employed to transfer a suitable volume of nucleic acid sample, e.g., 100 nl to 1 ml, from one or more wells of a sample plate to one or more nodes of the thermal chip module having an a volume of encapsulating fluid therein. The sample transfer head deposits a volume of nucleic acid sample into the node using a non-contact microfluidic dispensing protocol in a manner sufficient to produce a CLC having a sample core. Details regarding CLC production methods which may be employed by the device are further described in U.S. Pat. No. 8,465,707, the disclosure of which is herein incorporated by reference.

Following production of sample containing CLC node(s) in the thermal chip module(s), the bulk reagent dispenser dispenses common reagents into each CLC containing node. Common reagents that may be dispensed into the different nodes by the bulk reagent dispenser include, but are not limited to: dNTPs (e.g., in the form of a mastermix), enzymes, e.g., polymerases, primers, platform specific sequencing adaptors (which may or may not be integrated with the primers), etc. The bulk reagent dispenser may employ a non-contact microfluidic dispensing protocol in order to add the reagents to the CLCs. Each reagent may be sequentially added, or two or more reagents may be pre-combined and added to the CLCs, as desired. Following reagent addition to the CLCs in the nodes by the bulk reagent dispenser, the thermal chip modules may be subjected to temperature modulation, e.g., in the form of thermal cycling, as desired for a given NGS library preparation protocol.

Next, sample identifiers, e.g., nucleic acid barcodes, may be added to the nodes to uniquely identify the CLCs by sample source. In this step, the robotic liquid handler exchanges the sample dispense head for the barcode dispense head. The barcode dispense head is employed to transfer a volume of barcode reagent from a well of a barcode plate to a node of the thermal chip module having a sample containing CLC present therein. The barcode transfer head deposits a volume of barcode reagent into the node using a non-contact microfluidic dispensing protocol in a manner sufficient to produce a CLC having a sample core that includes a nucleic acid barcode.

The bulk reagent dispenser then dispenses ligase into each CLC containing node. The bulk reagent dispenser may employ a non-contact microfluidic dispensing protocol in order to add the ligase to the CLCs. Following ligase addition to the CLCs in the nodes by the bulk reagent dispenser, the thermal chip modules may be subjected to thermal cycling, as desired, e.g., to ligate the barcodes to the nucleic acid amplicons in the CLCs and thereby produce barcoded nucleic acid amplicons in the CLC.

Following production of the barcoded nucleic acid amplicons in the CLCs of the nodes of the thermal chip modules, the resultant barcoded nucleic acid amplicons may be purified to produce a product NGS library suitable for use in an NGS sequencing protocol. While the resultant barcoded amplicons may be purified using any convenient protocol, in some instances a magnetic bead based purification protocol is employed. In such a protocol, the purification head of the robotic liquid handler is exchanged for the barcode dispense head, and the purification head is employed to transfer a suitable quantity of magnetic beads, e.g., 100 nl to 1 ml, from one or more wells of a bead containing laboratory plate present on the shaker unit plate location to one or more nodes of the thermal chip module. The purification head deposits an amount of magnetic beads into the node using a non-contact microfluidic dispensing protocol in a manner sufficient to produce a CLC that includes magnetic beads. The beads are configured to specifically bind to barcoded nucleic acid amplicons in the CLC, e.g., via complementary nucleic acid domains that hybridize to each other. Following a suitable period of time for specific binding of barcoded nucleic acid amplicons to the beads, the purification head is used to retrieve the CLCs containing the nucleic acid bound beads from the nodes of the thermal chip modules and move the beads to a suitable purification location of the device. Once at the purification location of the device, the bead bound barcoded nucleic acid amplicons are washed and then separated from the beads using a sequential liquid contact protocol. In such a protocol, the magnetic beads are first immobilized at a location of a conduit of the purification head (e.g., an inner surface), e.g., by positioning the conduit next to a magnetic field. Next, a wash fluid is flowed past the immobilized beads, which removes CLC encapsulating fluid and other non-bead bound entities from the immobilized beads. Following washing, the bead bound nucleic acid amplicons may be released from the beads by flowing a suitable eluent liquid past the immobilized beads. The resultant released barcoded nucleic acid amplicons may then be collected, including pooled, into suitable receptacles positioned on the receptacle plate location, and are then ready for use in a NGS sequencing protocol. Details regarding magnetic bead/conduit based purification protocols that may be employed by the device are further described in PCT Application Serial No. PCT/IB2014/002159 published as WO 2014/207577; the disclosure of which is herein incorporated by reference.

The resultant product NGS libraries may then be sequenced, as desired, using any convenient NGS sequencing platform, including: the HiSeq™, MiSeq™ and Genome Analyzer™ sequencing systems from Illumina®; the Ion PGM™ and Ion Proton™ sequencing systems from Ion Torrent™; the PACBIO RS II sequencing system from Pacific Biosciences, the SOLiD sequencing systems from Life Technologies™, the 454 GS FLX+ and GS Junior sequencing systems from Roche, or any other convenient sequencing platform.

Computer Controllers

Aspects of the present disclosure further include computer controllers for operating the devices, where the controllers further include one or more computer elements for complete automation or partial automation of a device as described herein. In some embodiments, the controllers include a computer having a computer readable storage medium with a computer program stored thereon, where the computer program when loaded on the computer includes instructions for actuation the device to perform a CLC mediated NGS library production protocol, e.g., as described above.

In embodiments, the controller includes an input module, a processing module and an output module. Processing modules of interest may include one or more processors that are configured and automated to implement one or more routines of the device, e.g., as described above. For example processing modules may include two or more processors, such as three or more processors, such as four or more processors and including five or more processors, that are configured and automated to produce an NGS library. As described above, each processor includes memory having a plurality of instructions for performing the steps of the subject methods.

The controllers may include both hardware and software components, where the hardware components may take the form of one or more platforms, such that the functional elements, i.e., those elements of the controller that carry out specific tasks (such as managing input and output of information, processing information, etc.) of the controller may be carried out by the execution of software applications on and across the one or more computer platforms represented of the system.

Controllers may include a display and operator input device. Operator input devices may, for example, be a keyboard, mouse, or the like. The processing module includes a processor which has access to a memory having instructions stored thereon for performing the steps of the subject methods. The processing module may include an operating system, a graphical user interface (GUI) controller, a system memory, memory storage devices, and input-output controllers, cache memory, a data backup unit, and many other devices. The processor may be a commercially available processor or it may be one of other processors that are or will become available. The processor executes the operating system and the operating system interfaces with firmware and hardware in a well-known manner, and facilitates the processor in coordinating and executing the functions of various computer programs that may be written in a variety of programming languages, such as Java, Perl, C++, other high level or low level languages, as well as combinations thereof, as is known in the art. The operating system, typically in cooperation with the processor, coordinates and executes functions of the other components of the computer. The operating system also provides scheduling, input-output control, file and data management, memory management, and communication control and related services, all in accordance with known techniques.

The system memory may be any of a variety of known or future memory storage devices. Examples include any commonly available random access memory (RAM), magnetic medium such as a resident hard disk or tape, an optical medium such as a read and write compact disc, flash memory devices, or other memory storage device. The memory storage device may be any of a variety of known or future devices, including a compact disk drive, a tape drive, a removable hard disk drive, or a diskette drive. Such types of memory storage devices typically read from, and/or write to, a program storage medium (not shown) such as, respectively, a compact disk, magnetic tape, removable hard disk, or floppy diskette. Any of these program storage media, or others now in use or that may later be developed, may be considered a computer program product. As will be appreciated, these program storage media typically store a computer software program and/or data. Computer software programs, also called computer control logic, typically are stored in system memory and/or the program storage device used in conjunction with the memory storage device.

In some embodiments, a computer program product is described comprising a computer usable medium having control logic (computer software program, including program code) stored therein. The control logic, when executed by the processor the computer, causes the processor to perform functions described herein. In other embodiments, some functions are implemented primarily in hardware using, for example, a hardware state machine. Implementation of the hardware state machine so as to perform the functions described herein will be apparent to those skilled in the relevant arts.

Memory may be any suitable device in which the processor can store and retrieve data, such as magnetic, optical, or solid state storage devices (including magnetic or optical disks or tape or RAM, or any other suitable device, either fixed or portable). The processor may include a general purpose digital microprocessor suitably programmed from a computer readable medium carrying necessary program code. Programming can be provided remotely to processor through a communication channel, or previously saved in a computer program product such as memory or some other portable or fixed computer readable storage medium using any of those devices in connection with memory. For example, a magnetic or optical disk may carry the programming, and can be read by a disk writer/reader. Systems of the invention also include programming, e.g., in the form of computer program products, algorithms for use in practicing the methods as described above. Programming according to the present invention can be recorded on computer readable media, e.g., any medium that can be read and accessed directly by a computer. Such media include, but are not limited to: magnetic storage media, such as floppy discs, hard disc storage medium, and magnetic tape; optical storage media such as CD-ROM; electrical storage media such as RAM and ROM; portable flash drive; and hybrids of these categories such as magnetic/optical storage media.

The processor may also have access to a communication channel to communicate with a user at a remote location. By remote location is meant the user is not directly in contact with the system and relays input information to an input manager from an external device, such as a computer connected to a Wide Area Network ("WAN"), telephone network, satellite network, or any other suitable communication channel, including a mobile telephone (i.e., smartphone).

In some embodiments, controllers according to the present disclosure may be configured to include a communication interface. In some embodiments, the communication interface includes a receiver and/or transmitter for communicating with a network and/or another device. The communication interface can be configured for wired or wireless communication, including, but not limited to, radio frequency (RF) communication (e.g., Radio-Frequency Identification (RFID), Zigbee communication protocols, WiFi, infrared, wireless Universal Serial Bus (USB), Ultra Wide Band (UWB), Bluetooth® communication protocols, and cellular communication, such as code division multiple access (CDMA) or Global System for Mobile communications (GSM).

Output controllers may include controllers for any of a variety of known display devices for presenting information to a user, whether a human or a machine, whether local or remote. If one of the display devices provides visual information, this information typically may be logically and/or physically organized as an array of picture elements. A graphical user interface (GUI) controller may include any of a variety of known or future software programs for providing graphical input and output interfaces between the system and a user, and for processing user inputs. The functional elements of the computer may communicate with each other via system bus. Some of these communications may be accomplished in alternative embodiments using network or other types of remote communications. The output manager may also provide information generated by the processing module to a user at a remote location, e.g., over the Internet, phone or satellite network, in accordance with known techniques. The presentation of data by the output manager may be implemented in accordance with a variety of known techniques. As some examples, data may include SQL, HTML or XML documents, email or other files, or data in other forms. The data may include Internet URL addresses so that a user may retrieve additional SQL, HTML, XML, or other documents or data from remote sources. The one or more platforms present in the subject systems may be any type of known computer platform or a type to be developed in the future, although they typically will be of a class of computer commonly referred to as servers. However, they may also be a main-frame computer, a work station, or other computer type. They may be connected via any known or future type of cabling or other communication system including wireless systems, either networked or otherwise. They may be co-located or they may be physically separated. Various operating systems may be employed on any of the computer platforms, possibly depending on the type and/or make of computer platform chosen. Appropriate operating systems include Windows NT®, Windows XP, Windows 7, Windows 8, iOS, Sun Solaris, Linux, OS/400, Compaq Tru64 Unix, SGI IRIX, Siemens Reliant Unix, and others.

Notwithstanding the appended clauses, the disclosure set forth herein is also defined by the following clauses:

1. A complete nucleic acid library preparation device, the device comprising:
  a thermal chip module comprising multiple nodes;
  a plate location;
  a robotically controlled liquid handler configured to transfer liquid between the plate location and the thermal chip module;
  a bulk reagent dispenser configured to access each node of the thermal chip module.
2. The device according to Clause 1, wherein the device comprises a single thermal chip module.
3. The device according to Clause 1, wherein the device comprises only two thermal chip module.
4. The device according to any of Clauses 1 to 3, wherein each thermal chip module comprises 384 nodes.
5. The device according to any of Clauses 1 to 4, wherein the device comprises a mechanically actuated lid for each thermal chip module.
6. The device according to any of Clauses 1 to 5, wherein one of the plate locations is a shaker unit.
7. The device according to any of Clauses 1 to 6, wherein the device comprises six plate locations.
8. The device according to Clause 7, wherein the device comprises two sample plate locations.
9. The device according to Clauses 7 or 8, wherein the device comprises two barcode plate locations.
10. The device according to any of Clauses 1 to 9, wherein the robotically controlled liquid handler comprises interchangeable heads configured for sample dispense, barcode dispense, vacuum and purification tasks.
11. The device according to any of Clauses 1 to 10, wherein the device comprises a level control system configured to maintain carrier oil height within the thermal chip module(s).
12. The device according to any of Clauses 1 to 11, wherein the device comprises a fluidics module comprising liquid reservoirs for system fluids and waste collection.
13. The device according to Clause 12, wherein the waste collection reservoir is operatively coupled to a single waste drain.
14. The device according to any of Clauses 1 to 12, wherein the device is operatively coupled to a handheld barcode scanner.
15. The device according to any of Clauses 1 to 14, wherein the device is configured to produce 768 libraries via a composite liquid cell mediated protocol.
16. The device according to any of the preceding clauses, wherein the device is 0.805 m deep, 1.54 m long and 0.885 m high.
17. A nucleic acid library preparation device, the device comprising:
  a thermal chip module comprising multiple nodes; and
  a level control system configured to maintain carrier oil height within the thermal chip module.
18. The device according to Clause 17, wherein the device comprises a single thermal chip module.
19. The device according to Clauses 17 or 18, wherein the device comprises two thermal chip modules.
20. The device according to Clause 19, wherein the level control system is configured to maintain carrier oil height within each of the thermal chip modules.
21. The device according to any of Clauses 17 to 20, wherein each thermal chip module comprises 384 nodes.
22. The device according to any of Clauses 17 to 21, wherein the device comprises a mechanically actuated lid for each thermal chip module.
23. The device according to any of Clauses 17 to 22, wherein the device comprises one or more plate locations.
24. The device according to Clause 23, wherein one of the plate locations is a shaker unit.
25. The device according to Clauses 23 or 24, wherein the device comprises six plate locations.
26. The device according to Clause 25, wherein the device comprises two sample plate locations.
27. The device according to Clauses 25 or 26, wherein the device comprises two barcode plate locations.
28. The device according to any of Clauses 17 to 27, wherein the device comprises a robotically controlled liquid handler configured to transfer liquid between the two or more plate locations and the thermal chip module.
29. The device according to Clause 28, wherein the robotically controlled liquid handler comprises interchangeable heads configured for sample dispense, barcode dispense, reagent dispense, vacuum and purification tasks.
30. The device according to any of Clauses 17 to 29, wherein the device comprises a bulk reagent dispenser configured to access each node of the thermal chip module.
31. The device according to any of Clauses 17 to 30, wherein the device comprises a fluidics module comprising liquid reservoirs for system fluids and waste collection.
32. The device according to Clause 31, wherein the waste collection reservoir is operatively coupled to a single waste drain.
33. The device according to any of Clauses 17 to 32, wherein the device is operatively coupled to a handheld barcode scanner.
34. The device according to any of Clauses 17 to 33, wherein the device is configured to produce 768 libraries via a composite liquid cell mediated protocol.
35. The device according to any of Clauses 17 to 34, wherein the device is 0.805 m deep, 1.54 m long and 0.885 m high.
36. A method of producing a nucleic acid library from an initial nucleic acid sample, the method comprising:
  introducing the nucleic acid sample into a device according to any of Clauses 1 to 35; and
  obtaining the nucleic acid library from the device.
37. The method according to Clause 36, wherein the nucleic acid library comprises a barcoded nucleic acid library.
38. The method according to any of the Clauses 36 to 37, wherein the nucleic acid library comprises a pooled barcoded nucleic acid library.
39. A nucleic acid library produced according to the method of any of Clauses 36 to 38, wherein the nucleic acid library is configured for sequencing by a next generation sequencing protocol.

Although the foregoing invention has been described in some detail by way of illustration and example for purposes of clarity of understanding, it is readily apparent to those of ordinary skill in the art in light of the teachings of this disclosure that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A complete nucleic acid library preparation device, the device comprising:
   a thermal chip module comprising multiple nodes, each node comprising a wall defining a vessel, wherein each node is open both at the top and bottom;
   a lid for the thermal chip module;
   a plate location;
   a robotically controlled liquid handler configured to draw and dispense volumes of liquid to transfer liquid between the plate location and the thermal chip module;
   a bulk reagent dispenser distinct from the robotically controlled liquid handler and configured to access each node of the thermal chip module.

2. The device according to claim 1, wherein the device comprises only a single thermal chip module.

3. The device according to claim 1, wherein the device comprises only two thermal chip modules.

4. The device according to claim 1, wherein each thermal chip module comprises 384 nodes.

5. The device according to claim 3, wherein the device comprises a lid for each thermal chip module.

6. The device according to claim 1, wherein the device comprises six plate locations.

7. The device according to claim 6, wherein one of the plate locations is a shaker unit.

8. The device according to claim 7, wherein the device comprises two sample plate locations.

9. The device according to claim 7, wherein the device comprises two barcode plate locations configured to hold laboratory plates holding identifier nucleic acid barcode reagents.

10. The device according to claim 1, wherein the robotically controlled liquid handler comprises interchangeable heads configured for sample dispense, barcode dispense, vacuum and purification tasks.

11. The device according to claim 1, wherein the device comprises a level control system configured to maintain carrier oil height within the thermal chip module(s).

12. The device according to claim 1, wherein the device comprises a fluidics module comprising liquid reservoirs for system fluids and waste collection.

13. The device according to claim 12, wherein the waste collection reservoir is operatively coupled to a single waste drain.

14. The device according to claim 1, wherein the device is operatively coupled to a handheld barcode scanner.

15. The device according to claim 1, wherein the device is configured to produce 768 libraries via a composite liquid cell mediated protocol.

16. The device according to claim 1, wherein the device is 0.805 m deep, 1.54 m long and 0.885 m high.

17. A nucleic acid library preparation device, the device comprising:
   a thermal chip module comprising multiple nodes, each node comprising a wall defining a vessel, wherein each node is open both at the top and bottom;
   a lid for the thermal chip module;
   a robotically controlled liquid handler configured to draw and dispense volumes of liquid to transfer liquid between a plate location and the thermal chip module; and
   a level control system configured to maintain carrier oil height within the thermal chip module.

18. A method of producing a nucleic acid library from an initial nucleic acid sample, the method comprising:
   introducing the nucleic acid sample into a device according to claim 1; and
   obtaining the nucleic acid library from the device.

19. The method according to claim 18, wherein the nucleic acid library comprises a barcoded nucleic acid library.

20. The device according to claim 1, wherein the thermal chip module comprises a node-defining plate.

21. The device according to claim 20, wherein the thermal chip module comprises a common carrier liquid reservoir below the node-defining plate.

22. The device according to claim 1, wherein the lid is a mechanically actuated lid.

* * * * *